(12) United States Patent
Schouenborg

(10) Patent No.: US 10,315,027 B2
(45) Date of Patent: Jun. 11, 2019

(54) MEDICAL MICROELECTRODE, METHOD FOR ITS MANUFACTURE, AND USE THEREOF

(71) Applicant: NEURONANO AB, Karlshamn (SE)

(72) Inventor: Jens Schouenborg, Lund (SE)

(73) Assignee: NEURONANO AB (SE)

( * ) Notice: Subject to any disclaimer, the term of this patent is extended or adjusted under 35 U.S.C. 154(b) by 642 days.

(21) Appl. No.: 14/408,541

(22) PCT Filed: Jun. 19, 2013

(86) PCT No.: PCT/SE2013/000101
§ 371 (c)(1),
(2) Date: Dec. 16, 2014

(87) PCT Pub. No.: WO2013/191612
PCT Pub. Date: Dec. 27, 2013

(65) Prior Publication Data
US 2015/0151107 A1    Jun. 4, 2015

(30) Foreign Application Priority Data

Jun. 21, 2012  (SE) .................................. 1200373

(51) Int. Cl.
| | |
|---|---|
| *A61B 5/04* | (2006.01) |
| *A61N 1/05* | (2006.01) |
| *A61B 18/00* | (2006.01) |
| *A61B 18/14* | (2006.01) |
| *A61M 31/00* | (2006.01) |

(52) U.S. Cl.
CPC ............ *A61N 1/05* (2013.01); *A61B 5/04001* (2013.01); *A61B 18/14* (2013.01); *A61M 31/002* (2013.01);
(Continued)

(58) Field of Classification Search
CPC ........................... A61B 18/14; A61B 5/04001
(Continued)

(56) References Cited

U.S. PATENT DOCUMENTS

| | | |
|---|---|---|
| 5,902,329 A | 5/1999 | Hoffmann et al. |
| 7,801,624 B1 * | 9/2010 | Flannery .............. A61N 1/0575 |
| | | 607/116 |

(Continued)

FOREIGN PATENT DOCUMENTS

| | | |
|---|---|---|
| WO | WO 98/17995 A1 | 4/1998 |
| WO | WO 00/01300 A1 | 1/2000 |

(Continued)

OTHER PUBLICATIONS

International Search Report dated Oct. 9, 2013 issued in corresponding International patent application No. PCT/SE2013/000101.

*Primary Examiner* — Amanda K Hulbert
*Assistant Examiner* — Philip C Edwards
(74) *Attorney, Agent, or Firm* — Ostrolenk Faber LLP

(57) ABSTRACT

A proto microelectrode from which a micro electrode is formed in situ upon insertion into soft tissue comprises a flexible oblong electrode body of electrically conducting material having a front end and a rear end. The electrode body having a metal or a metal alloy or an electrically conducting form of carbon or an electrically conducting polymer or a combination thereof. A first coat of a water soluble and/or swellable and/or degradable material is disposed on the electrode body and extends along is at least over a distal portion thereof. A second coat of electrically insulating, water insoluble flexible polymer material is disposed on the first coat. The second coat comprises one or more through openings at or near its front end. Also disclosed is a corresponding micro electrode and a method of manufacture.

28 Claims, 16 Drawing Sheets

(52) U.S. Cl.
CPC ......... *A61N 1/0536* (2013.01); *A61N 1/0558* (2013.01); *A61B 2018/00071* (2013.01); *A61B 2018/00107* (2013.01); *A61B 2018/00434* (2013.01)

(58) Field of Classification Search
USPC ........................................................ 600/377
See application file for complete search history.

(56) References Cited

U.S. PATENT DOCUMENTS

| | | | | |
|---|---|---|---|---|
| 2005/0085886 | A1* | 4/2005 | Hess | A61N 1/0575 607/127 |
| 2010/0324637 | A1* | 12/2010 | Trip | A61N 1/057 607/116 |
| 2011/0009728 | A1* | 1/2011 | Schouenborg | A61N 1/0551 600/373 |
| 2011/0288547 | A1 | 11/2011 | Morgan et al. | |

FOREIGN PATENT DOCUMENTS

| | | |
|---|---|---|
| WO | WO 01/43815 A1 | 6/2001 |
| WO | WO 2006/118641 A1 | 2/2006 |
| WO | WO 2007/040442 A1 | 4/2007 |
| WO | WO 2007/134315 A1 | 11/2007 |
| WO | WO 2007/143303 A2 | 12/2007 |
| WO | WO 2008/107815 A1 | 9/2008 |
| WO | WO 2009/075625 A1 | 6/2009 |
| WO | WO 2010/144016 A1 | 12/2010 |
| WO | WO 2011/047148 A2 | 4/2011 |

\* cited by examiner

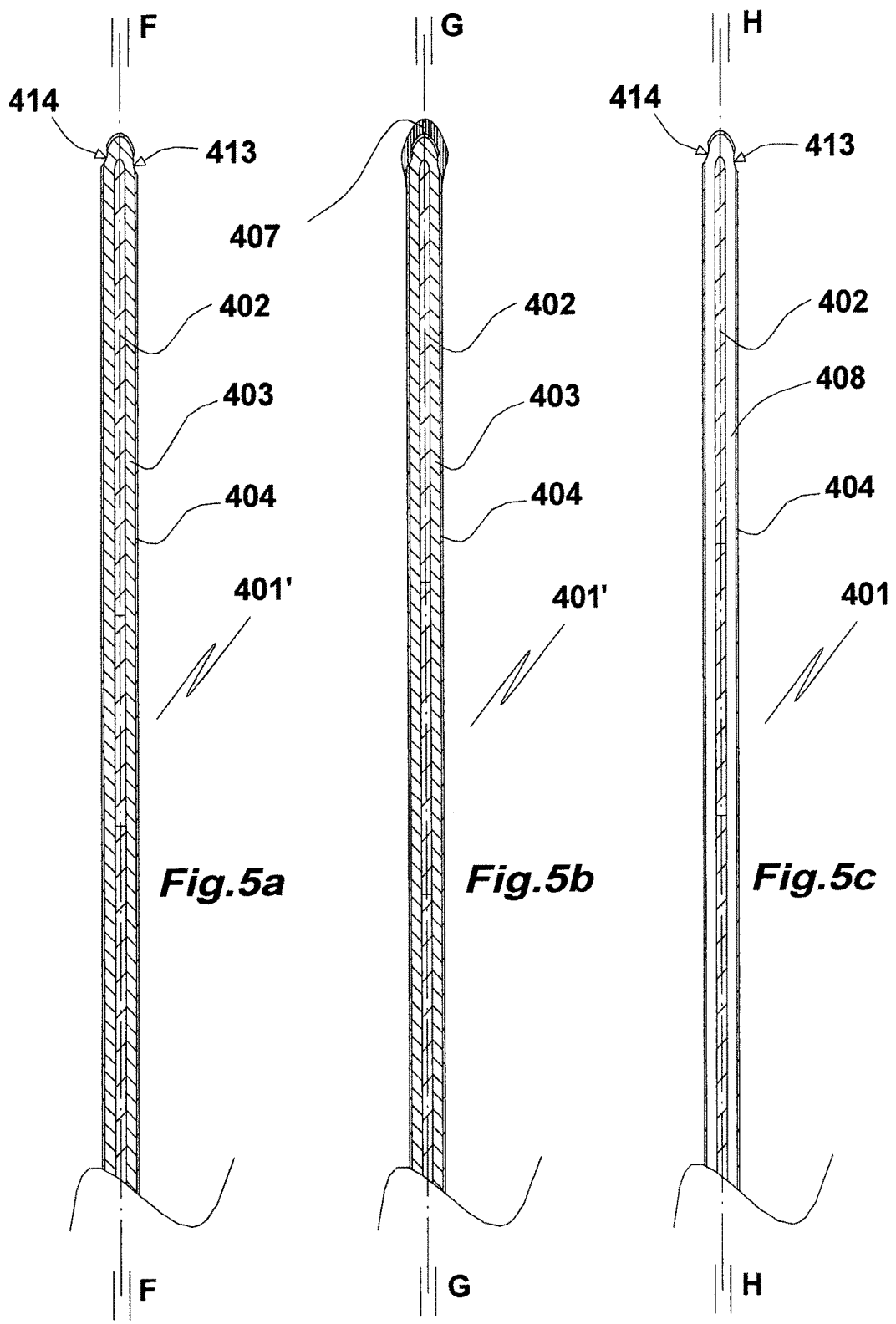

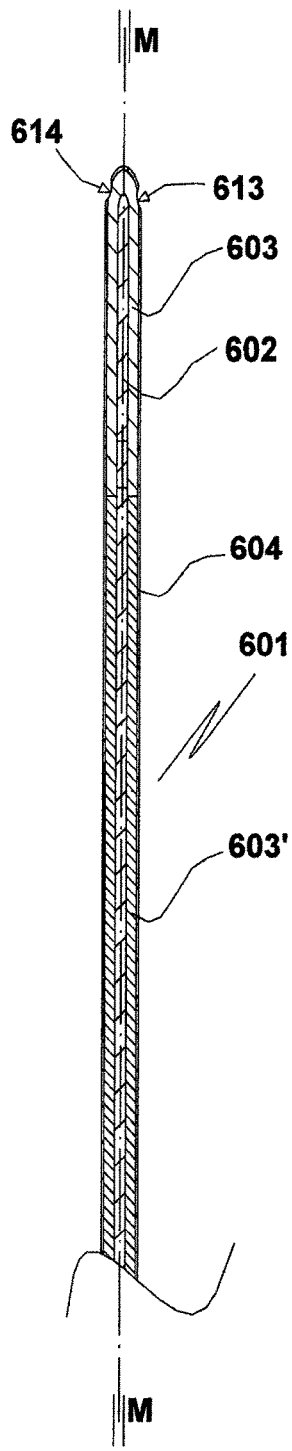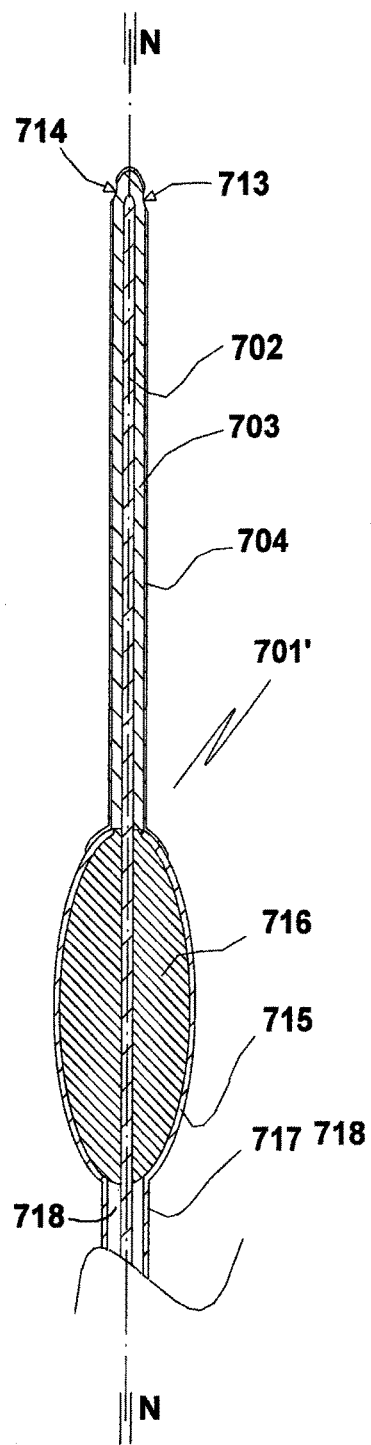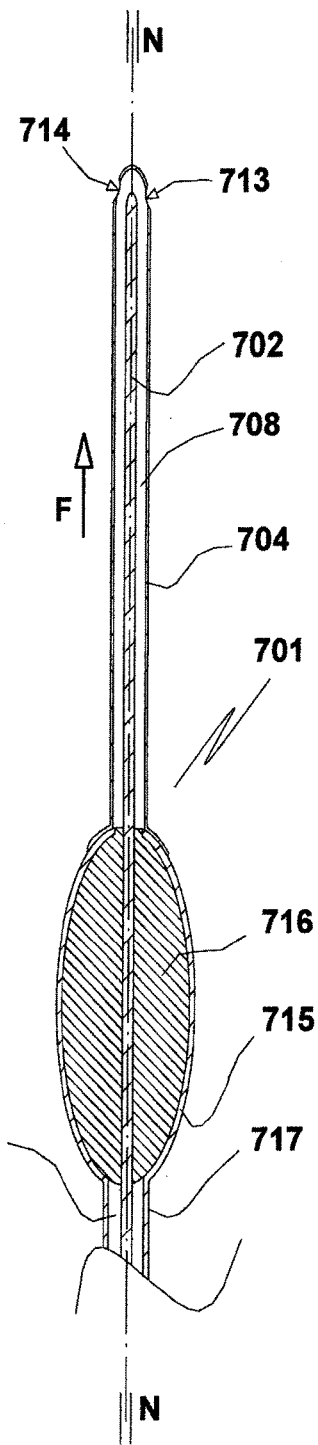
*Fig.9*  *Fig.10a*  *Fig.10b*

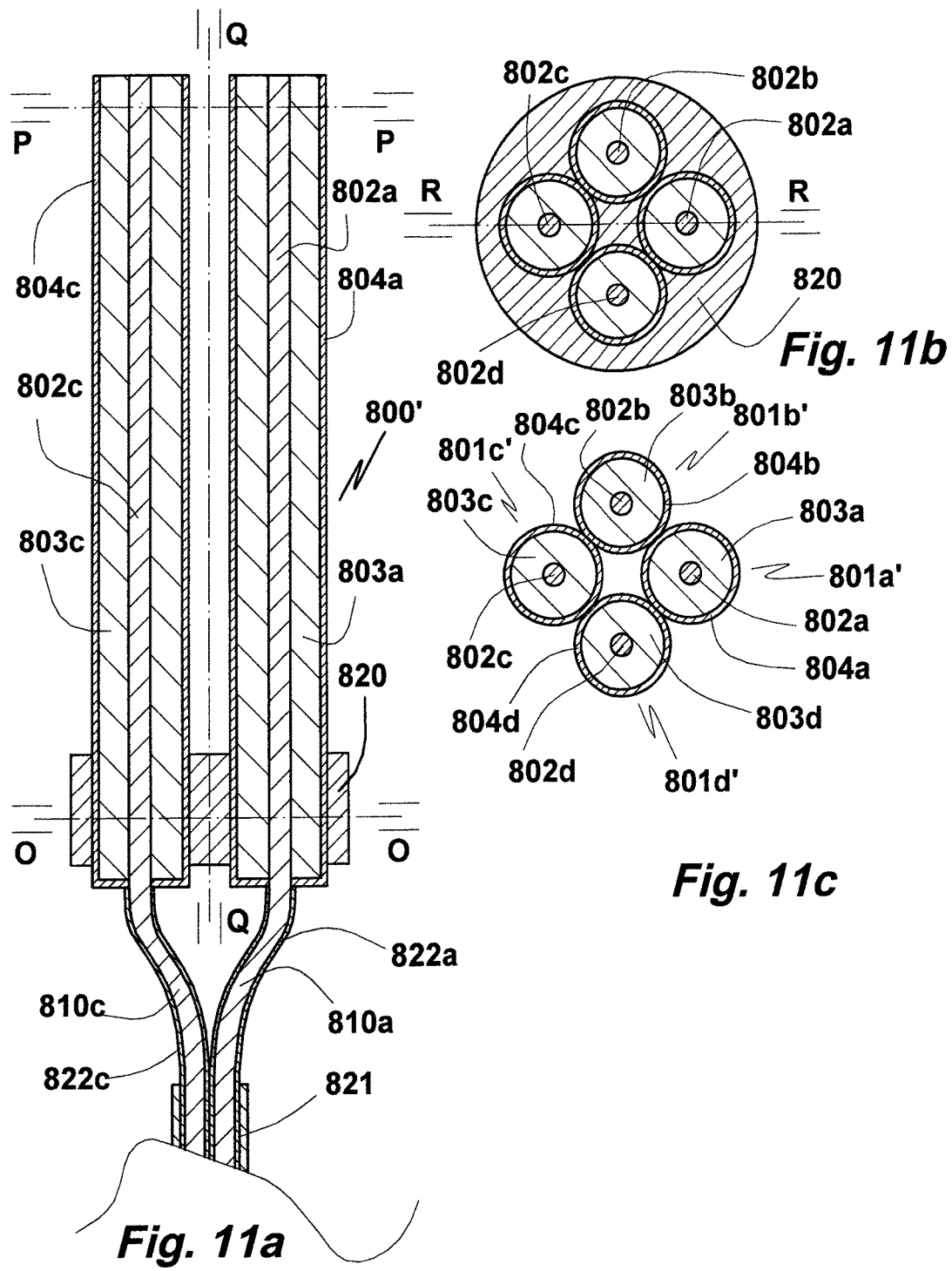

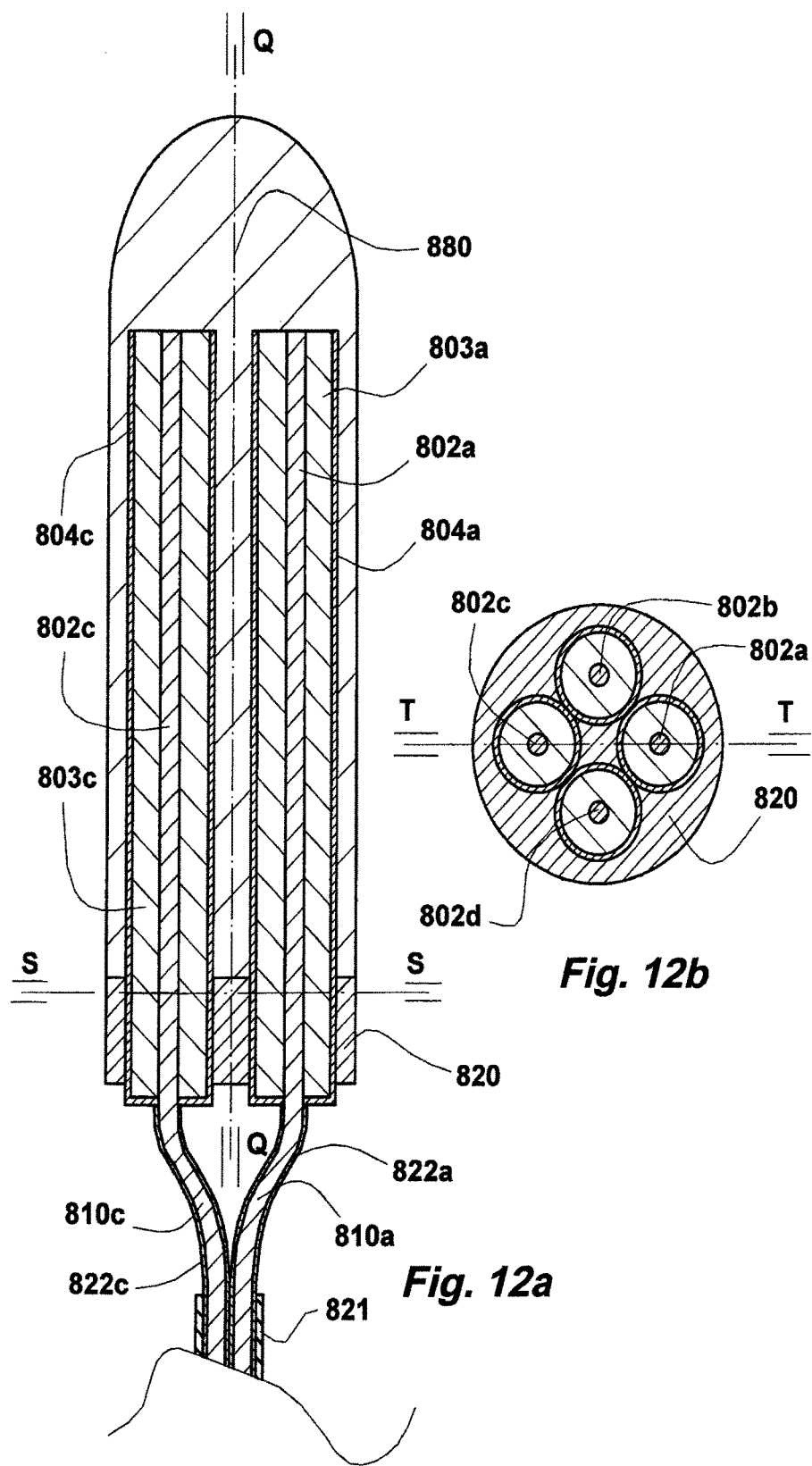

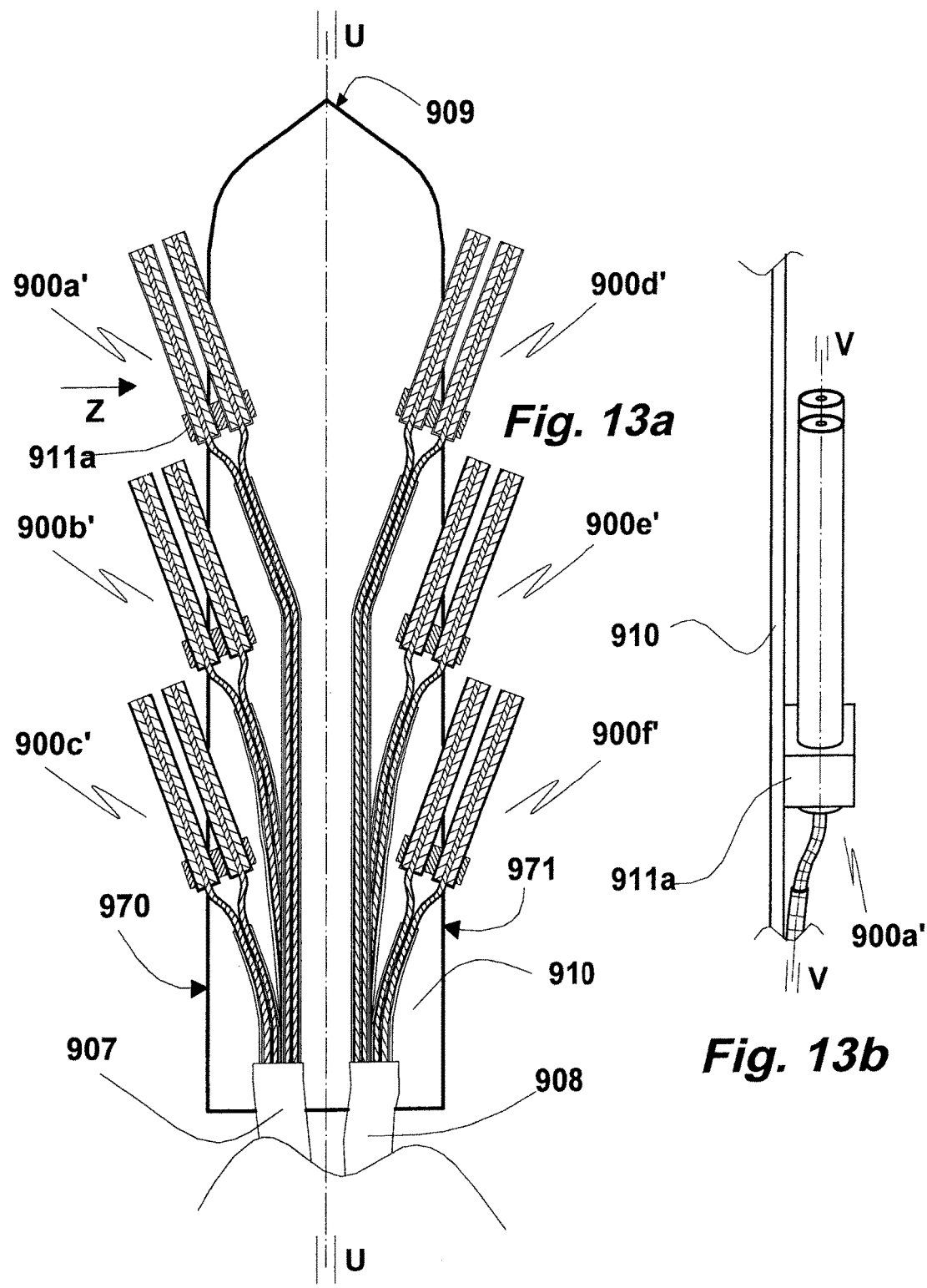

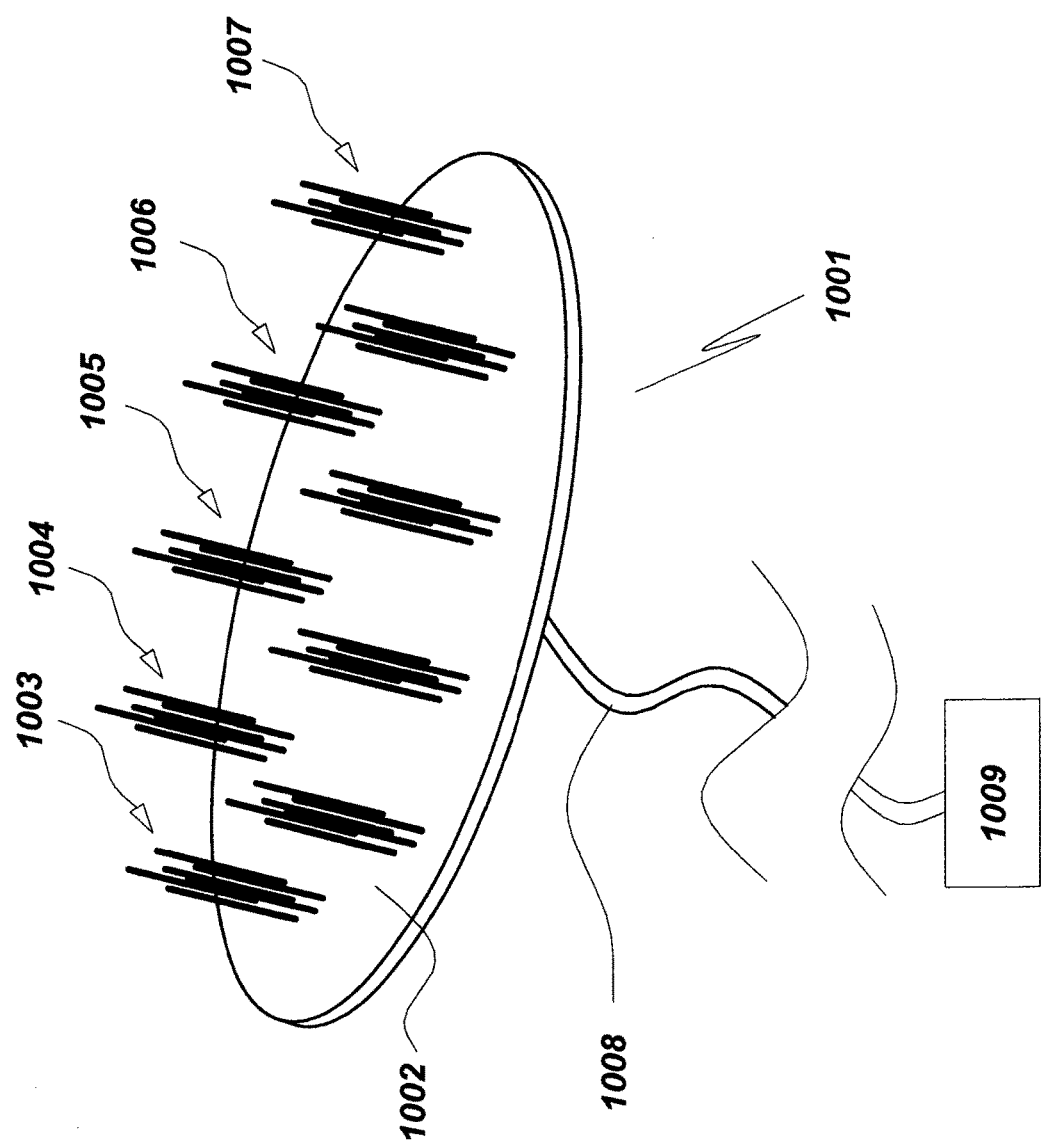

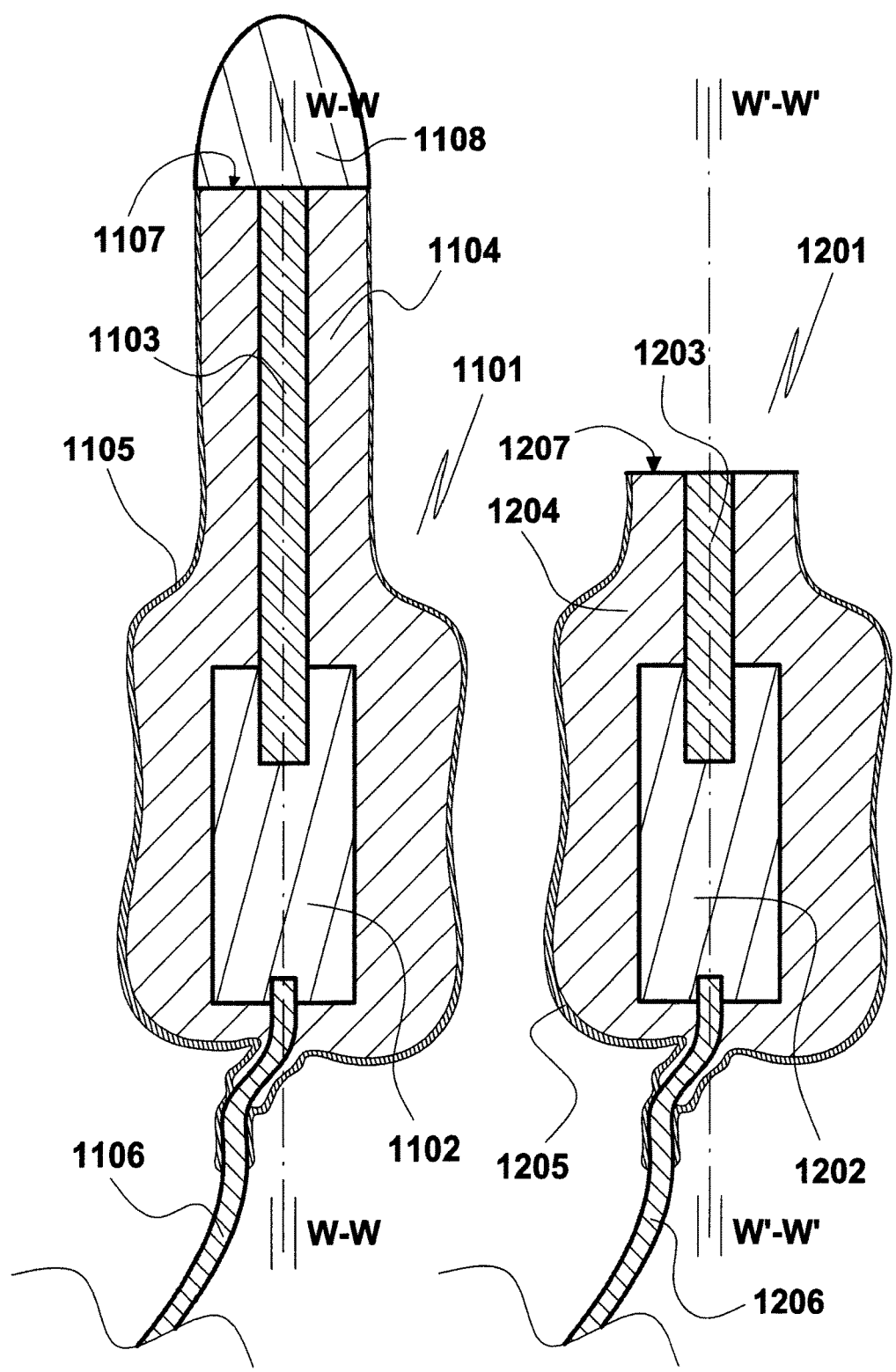
*Fig. 15*   *Fig. 16*

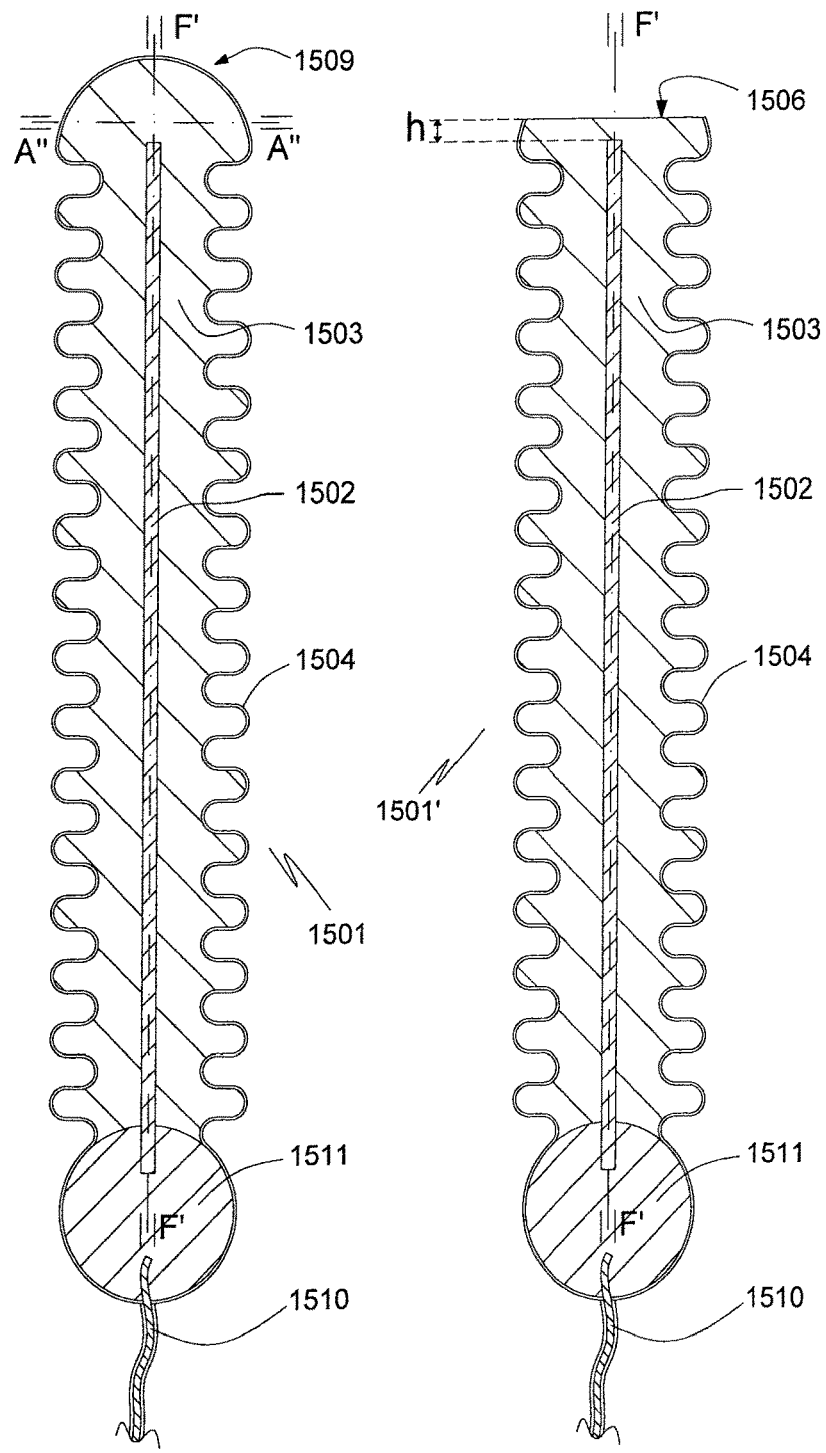
*Fig. 19a*  *Fig. 19b*

MEDICAL MICROELECTRODE, METHOD FOR ITS MANUFACTURE, AND USE THEREOF

CROSS REFERENCE TO RELATED APPLICATIONS

The present application is a 35 U.S.C. § 371 National Phase conversion of PCT/SE2013/000101, filed Jun. 19, 2013, which claims benefit of Swedish Application No. 1200373-7, filed Jun. 21, 2012, the disclosures of which are incorporated herein by reference. The PCT International Application was published in the English language.

FIELD OF THE INVENTION

The present invention relates to a medical proto microelectrode for full or partial disposition in soft tissue, to a microelectrode so disposed, to a method of producing the proto microelectrode, and to its use. Furthermore the present invention relates to bundles and arrays comprising two or more proto electrodes of the invention and to corresponding micro electrode bundles and arrays disposed fully or partially in soft tissue.

BACKGROUND OF THE INVENTION

Microelectrodes for implantation into soft tissue, in particular tissue of the central nervous system (CNS), have a wide field of application (Brain Machine Interfaces. Implications for Science, Clinical Practice and Society. Schouenborg J, Garwicz M and Danielsen N, Eds. Progress in Brain Research, Elsevier Science Ltd. 2011, ISBN 13: 978-0-444-53815-4). In principle, all brain nuclei can be recorded from or stimulated by such electrodes and their functions monitored. Of particular interest are multichannel electrodes for brain nuclei stimulation. In multichannel electrode design, groups of electrodes or even individual electrodes can be addressed separately. This allows a user to select those electrodes whose stimulation produces a therapeutic effect that is improved in comparison with non-selective stimulation. Stimulation of the brain or spinal cord can be of particular value in situations when brain nuclei are degenerated or injured. A multichannel design may provide for efficient measurement of the effects of systemic or local drug administration or gene transfer on neurons of the brain and spinal cord. Monitoring brain activity through implanted electrodes can be used to control drug delivery locally or systemically or to control electrical stimulation of brain nuclei. Furthermore, multichannel electrodes may be used to lesion specific sites in tissue upon detection of abnormal electric activity by the same electrodes.

An implanted microelectrode should affect the adjacent tissue as little as possible. Since the brain, the spinal cord, and peripheral nerves exhibit considerable movements caused by body movements, heart beats, and respiration, it is important that an implanted electrode can follow the movements of the tissue with as little as possible displacement relative to target tissue. To this end an implanted electrode should be resiliently flexible. Different methods to implant flexible electrodes are known in the art. For example, ultrathin and flexible electrodes, which are difficult or impossible to implant as such, can be implanted after embedding them in a hard matrix, which provides necessary support during implantation. After implantation the matrix is dissolved by tissue fluid. A requirement for successful implantation is the use of a biocompatible matrix material.

A problem with microelectrodes known in the art is that most of their impedance is made up by the impedance at the electrode/body fluid boundary. When current is passed through a medical electrode into or out from tissue, the current density is not uniform over a microelectrode surface, being substantially higher at edges, tips and surface irregularities than elsewhere. High local current densities cause the temperature to rise locally, and may even result in hydrolysis of aqueous tissue fluid. Soft tissue adjacent to sites of high current density thus risks to be irreversibly damaged.

To record activity in single neurons, the portion of the electrode in electrical contact with tissue and/or tissue fluid should be as small as possible. Since electrode impedance depends, to a large extent, on the surface area of that portion, various means have been developed to enlarge the surface to reduced electrode impedance. Methods for enlarging the electrically conducting surface area of electrodes are known by the art; they include roughening the surface mechanically or chemically coating the electrodes or coating with nanofibers of an electrically conductive polymer such as poly(3, 4-ethylenedioxythiophene; PEDOT or PEDT), platinum black or carbon nanotubes. A problem with such coats is that they easily detach from the electrode body and/or that they get covered and/or clogged upon implantation by biological material emanating from tissue and body fluid. Thereby, the surface area of the conductor is reduced resulting in an undesired change of impedance.

OBJECTS OF THE INVENTION

A primary object of the invention is to provide a microelectrode of the aforementioned kind for stimulating single nerve cells or groups of nerve cells, in which the risk of uncontrolled tissue damage by local high current density is substantially reduced or even nil, independent of whether the microelectrode is a single microelectrode or pertains to a bundle or an array of microelectrodes.

Another object of the invention is to provide a method for producing such a microelectrode.

Still another object of the invention is to provide a microelectrode of the aforementioned kind in which the risk of uncontrolled tissue damage by local high current density is substantially reduced or even nil, and which is easy to insert into soft tissue.

Further objects of the invention will become apparent from the following summary of the invention, the description of preferred embodiments thereof illustrated in a drawing, and from the appended claims.

SUMMARY OF THE INVENTION

In this application "electrode" signifies "microelectrode". "Water insoluble" signifies insoluble in aqueous body fluid, that is, interstitial or extracellular fluid but also serum. "Flexible" signifies a degree of flexibility that does not substantially impede a lateral movement of a microelectrode body of the invention. "Electrically insulating" signifies electrically insulating at voltages/currents used in treating of human nerve tissue. "Oblong" signifies a structure of a length greater by a factor of five or more, in particular of ten or more, than its diameter. "Swellable" means an expansion of volume by a factor of at least 1.2 at contact with aqueous body fluid. "Porous" signifies permeable for aqueous body fluids and biomolecules dissolved therein. As will be explained below in more detail "microelectrode" signifies a microelectrode of the invention in a state inserted into soft tissue and partially or fully equilibrated with body fluid in the tissue, whereas "proto microelectrode" and "proto electrode" signifies a corresponding microelectrode of the invention prior to insertion into the tissue.

According to the present invention is disclosed a microelectrode of the aforementioned kind, which solves or at least reduces one or more of the problems associated with microelectrodes known in the art. The microelectrode of the invention is formed upon insertion of a corresponding proto microelectrode into soft tissue and equilibration with aqueous body fluid in the tissue. The microelectrode of the invention substantially reduces the risk of tissue damage by local high current density. In the microelectrode of the invention soft tissue adjacent to the electrode is shielded from the heat generated at or near the surface of the electrically conducting electrode body or element thereof by a column of body fluid and a flexible, electrically insulating barrier of water insoluble polymer surrounding the electrode body and the column of body fluid. On the other hand, the electrode body, in particular an electrode body with an enlarged surface thereof, such as a physically and/or chemically roughened surface, or a surface provided with nanostructured elements, for instance mono-crystalline metal outgrowths, is protected from contact with living cells, such as phagocytes, in particular microglia.

The microelectrode of the invention comprises or substantially consists of a flexible oblong, electrically conducting electrode body having a front (distal) end and a rear (proximal) end, the electrode body comprising or consisting of a metal or a metal alloy or an electrically conducting form of carbon or an electrically conducting polymer or a combination thereof, a (second) coat of electrically insulating, water insoluble and flexible, preferably also resiliently flexible, polymer material surrounding the electrode body over its entire length or at least over a portion extending from its front end towards its rear end and disposed at a distance from the electrode body so as to define a tubular interstice filled with aqueous body fluid and/or with a gel comprising aqueous body fluid. The electrode of the invention is preferably rotationally symmetric in respect of its central axis extending from the front end to the rear end.

Furthermore, according to the present invention, is disclosed a proto microelectrode from which the electrode of the invention is formed in situ upon insertion of the proto microelectrode into soft tissue. The proto electrode of the invention comprises or substantially consists of a flexible oblong electrode body of electrically conducting material having a front (distal) end and a rear (proximal) end, the electrode body comprising or consisting of a metal or a metal alloy or an electrically conducting form of carbon or an electrically conducting polymer or a combination thereof, a first coat of a water soluble and/or swellable and/or degradable material on the electrode extending along the electrode body at least over a portion extending from its front end towards its rear end, and a second coat of electrically insulating, water insoluble flexible polymer material on the first coat, the second coat comprising one or more through openings at or near the front end. Upon insertion of the proto electrode of the invention into soft tissue the electrode of the invention is formed by the action of aqueous body fluid on the first coat, which is dissolved and/or degraded and/or swollen. Access of aqueous body fluid to the first coat is provided by said one or more through openings in the second coat. The material of the first coat can be one which is readily soluble in aqueous body fluid, such as glucose, or one which is not readily soluble in aqueous body fluid, such as glucose acetate, or one of intermediate solubility, such as partially acetylated glucose. A material of the first coat of a desired dissolution rate can also be obtained by combining materials of different solubility and/or dissolution properties, such as a combination of a low molecular carbohydrate and a peptide or protein, for instance the combination of glucose and gelatin. The first coat is preferably rotationally symmetric around a central axis, which preferably coincides with a central longitudinal axis of the electrode body. The proto electrode of the invention is preferably rotationally symmetric in respect of its central axis extending from its front end to its rear end.

According to an advantageous aspect of the invention surface areas of the first coat not covered by the second coat, that is, surface areas of the first coat accessible through said one or more through openings in the second coat, can be coated with a third coat of a biocompatible material soluble in aqueous body fluid retarding access of aqueous body fluid to the first coat. This delay allows the proto electrode of the invention to be correctly positioned in tissue prior to the start of dissolution of the first coat. A suitable third coat material is shellack or Kollicoat® IR (polyvinyl alcohol polyethylene glycol graft copolymer; BASF, Ludwigshafen, Germany). The third coat may alternatively comprise or consist of a material forming a gel at contact with aqueous body fluid; this gel is dissolved and/or degraded only slowly, that is, over hours and days or even weeks and months, such as from one day to one week or from one week to four weeks or even from one month to a year or more. The dissolution or degradation rate of the gel can be controlled by cross-linking, the dissolution/degradation rate decreasing with increased cross-linking. A suitable material for this purpose is gelatin cross-linked with EDC (1-(3-dimethylaminopropyl)-3-ethylcarbodiimide). The gel has pores of a size allowing small molecules, such as dissolved material from the first coat, to pass through it by diffusion, and allowing small molecules in aqueous body fluid, such as low molecular weight peptides and salts to pass through it from surrounding body fluid into the fluid disposed in the interstice between the electrode body and the second coat. The gel can prevent the one or several through openings in the second coat from becoming clogged by tissue debris, for example cells or cell particles injured or formed by the implant.

The front end of the electrode body coincides or about coincides with the front end of the electrode or the proto electrode and front end of the second coat of flexible, water insoluble polymer. The rear end of the electrode body can coincide with the rear end of the electrode or extend further in a proximal direction, such further extension, while materially integral with the electrode body, not being considered to be comprised by the electrode proper but to serve as an electrical lead connecting the electrode with an electrode control unit. Alternatively, a separate lead is provided between the rear end of the electrode body to which it is soldered or otherwise joined in an electrically conducting manner, and an electrode control unit disposed at a distance from the electrode intra-corporeally or extra-corporeally. The separate lead or the lead integral with the electrode body extending proximally from the electrode is electrically insulated. The oblong flexible electrode body can correspond to, for instance, a functionally equivalent element in a microelectrode known in the art, such as in WO 2010/144016 A1 and WO 2007/040442 A1.

If the second coat of water insoluble flexible polymer material does not extend to the rear end of the electrode body the portion thereof not covered by the second coat is electrically insulated by other means, for instance by a water insoluble lacquer.

The water insoluble flexible, preferably resilient, polymer material of the second coat has a preferred wall thickness that is substantially smaller than the diameter of the electrode body and the wall thickness of the first coat, such as by a factor of five or even ten or more. A preferred thickness of the electrode body of the proto electrode and the corresponding electrode of the invention is from 1 µm to 100 µm or more, in particular from 2 µm to 10 µm or 25 µm or 40 µm, the wall thickness of the first coat being within the same range, while a preferred thickness of the second coat is in the range of a few µm, such as from 2 µm to 5 µm but even up to 20 µm or more. However, in certain applications in which a very thin electrode body is used, the wall thickness of the second coat can be larger than the diameter of the electrode body, such as by a factor of 2 or 10 or more.

The second coat must be biocompatible and sufficiently flexible to allow it to flex with the electrode body, in particular without restraining flections of the electrode body. The second coat is preferably resiliently flexible, in particular if the material of the first coat is one that swells in contact with aqueous body fluid, independent of whether it is later dissolved or degraded or not. Resilience of the second coat thus can prevent its rupture possibly be caused by the expansion of the first coat on contact with aqueous body fluid. A particularly preferred insulating polymer material of the second coat is a Parylene, such as Parylene C. Other preferred insulating materials comprise polytetrafluoroethene, polyurethane, polyimide, various kinds of silicones and synthetic or natural rubber. The insulating polymer coat has a minimum thickness that provides sufficient electrical insulation. For Parylene C a minimum thickness of 2-5 µm is adequate in many applications. In congruence with the first coat, the second coat is preferably rotationally symmetric around a central axis shared with the first coat, that is, the second coat is preferably cylindrical or at least a portion intermediate between its front and rear portions is cylindrical.

According to a preferred aspect of the invention at least a portion of the second coat intermediate between its front and rear portions has the form of a bellows tube. The bellows tube portion is preferably rotationally symmetric around a central axis shared with the first coat.

According to an important aspect of the invention the bellows impart radial stability to the second coat upon dissolution of the first coat. At the same time, they provide a measure of extendibility/compressibility of the second coat in an axial direction. Furthermore, the bellows do not prevent portions of the no longer supported second coat from being bent away from the central longitudinal axis.

According to a still further aspect of the invention the provision of a second coat comprising bellows shaped portions provides improved anchoring capability for the electrode of the invention in comparison with that of an electrode with a cylindrical second coat.

According to another preferred aspect of the invention the proto electrode and, hence, the electrode of the invention comprise one or more anchoring elements extending from the electrode body for a short distance, such as for a distance corresponding to a tenth or less, preferably a twentieth or less, most preferred for a fiftieth or less, in particular a hundredth or less of the electrode body length. It is preferred for the anchoring element(s) to extend from the electrode body in an oblique proximal direction.

Once the proto electrode of the invention has been inserted into soft tissue, portions of the first coat not covered by the second coat and disposed at or near the front end allow the water dissolvable/swellable/degradable material of the second coat to be contacted by body fluid and start to be dissolved and/or degraded and/or start to swell. The dissolution and/or degradation and/or swelling of the first coat thus proceeds from the front end of the electrode body towards the rear end thereof. Through the opening(s) in the second coat the dissolved and/or degraded material of the first coat diffuses out from the tubular void formed between the electrode body and the second coat. By continuing exchange of fluid in the void with surrounding body fluid caused by diffusion, the void becomes filled with increasingly pure body fluid. By this process, the stiffened electrode body of the proto electrode of the invention is transformed into the flexible electrode body of the electrode of the invention capable of adapting to movements of surrounding tissue. Since the electrically insulating polymer coat has been designed to be thin and flexible it does not substantially restrict the movements of the electrode body but flexes with it. While the provision of a water swellable but not dissolvable material such as cross linked polyvinylpyrrolidone as a material for the first coat restricts, to a certain extent, flexing movements of the electrode body and the second coat, its content of aqueous body fluid provides for proper electrical electrode function.

The body fluid in which the first coat is preferably dissolvable but may also be degradable or capable of swelling in contact with an aqueous fluid, in particular an aqueous body fluid. While it is conceivable that, depending on the particular tissue receiving the proto electrode, the body fluid is a fluid rich in lipids or substantially consisting of lipids, such a fluid would not be capable of dissolving or swelling or degrading the first coat. For such an application, a first coat of lipid dissolvable or degradable material would have to be provided. For proper function the body fluid filling the tubular void upon dissolution or degradation of the lipid dissolvable or degradable material must however comprise sufficient aqueous body fluid phase to allow the electrode to fulfill its function.

According to a preferred aspect of the invention, the first coat can comprise one or more pharmacologically active agents. Pharmacologically active agents of the invention comprise or consist of agents influencing the function of nerve synapses like dopamine, serotonin, neuroleptics, sedatives, analgesics, agents exerting a trophic effect on nerve cells, for instance NGF, and gene vectors for long term effect. Other useful pharmacologically active agents include anti-inflammatory agents, anticoagulants, β-receptor blockers, antibodies and nutrients. In principle, any pharmacologically active agent of interest can be used, provided that it is sufficiently soluble in aqueous body fluid.

The first coat can also comprise two or more sections, in particular sections extending along different portions of the electrode body so as to join each other in a plane perpendicular to the central axis of a cylindrical or otherwise rotationally symmetric electrode body. The sections may differ in their solubility and/or swelling and/or degradation properties in aqueous body fluid and/or in their content of pharmacologically active agent(s).

According to a preferred aspect the proto electrode and the electrode of the invention comprises a drug reservoir compartment disposed at its rear end or proximal to its front end. At its front end the drug reservoir compartment of the electrode of the invention is in fluid communication with the tubular column of body fluid accumulated in the interstice between the electrode body and the second coat. At its rear end the drug reservoir may be connected to a conduit through which aqueous fluid such as saline can be adduced to the compartment. Alternatively such a conduit can be arranged to directly communicate with said interstice, and be used for adducing aqueous fluid to the interstice and from there to the surrounding tissue. The aqueous fluid thus provided to the electrode of the invention may contain any suitable pharmacologically active agent soluble therein.

According to another preferred aspect two electrodes of the invention are used in combination to provide bipolar stimulation. For this purpose two proto electrodes of the invention disposed in parallel and abutting each other are joined at the exterior face of their second coats by gluing or by enclosing them in a third flexible polymer coat, for instance of parylene C. The glue may be of same material as the second coat, such as of a parylene, or of a different material.

According to the present invention is disclosed a proto microelectrode prestage from which the proto microelectrode of the invention can be manufactured. The proto microelectrode prestage of the invention comprises or substantially consists of a flexible oblong electrode body of electrically conducting material having a front (distal) end and a rear (proximal) end, comprising or consisting of a metal or a metal alloy or an electrically conducting form of carbon or an electrically conducting polymer or a combination thereof, a first coat of water soluble and/or swellable and/or degradable material on the electrode body and extending along the body at least over a portion extending from its front end towards its rear end, and a second coat of water insoluble flexible polymer material on the first coat. The proto microelectrode prestage can be manufactured, for instance, by providing an oblong electrode body comprising or consisting of a metal or a metal alloy or an electrically conducting form of carbon or an electrically conducting polymer or a combination thereof, coating the electrode body with a water soluble and/or degradable and/or swellable material to form a first coat, then coating the first coat with a second coat of electrically insulating, flexible, preferably resilient, water insoluble polymer material. According to an advantageous aspect of the invention the proto microelectrode can comprise a third coat on its second coat. The material of the third coat is soluble in body fluid. It is preferred for the third coat to extend from the rear end of the proto microelectrode to the front end thereof, and to fully cover the front end. The aim with providing a third coat is to reinforce the proto electrode to avoid breaking it during insertion into soft tissue.

The proto microelectrode of the invention can be manufactured from the proto microelectrode prestage by cutting it in a radial plane, preferably near its front end. "Radial plane" is a plane perpendicular to the central axis of the proto microelectrode prestage. The cut off front end cap is discarded and the proto microelectrode of the invention is retained. Alternatively to cutting out portion(s) of the water insoluble flexible layer disposed near the front end second coat material can be removed by abrasion or other means, such as laser milling, to produce openings in the second coat.

According to a preferred aspect of the invention the proto microelectrode is cut transversally in a radial plane disposed distally of the front end of the electrode body. The electrode body of an electrode of the invention formed from a proto microelectrode cut in this manner is disposed somewhat withdrawn from the front end of the second coat in a proximal direction, that is, withdrawn into the volume defined by the second coat; this will provide additional protection from the electrode body coming into contact with soft tissue and damaging the tissue.

According to another preferred aspect of the invention, a proto microelectrode prestage can be manufactured by providing a negative mold corresponding to a desired form of the first coat, centering the electrode body in the mold, and filling the mold with a solution and/or suspension of the first coat material. It is preferred for the solution and/or suspension of the first coat material to comprise a gelling agent such as gelatin or gelling PEG. Alternatively or additionally, the mold is made of a microporous material to allow drying of the first coat material in the mold. After removal of the mold the second coat is applied on the first coat by, for instance, dipping the first coat/electrode body combination into a solution of the second coat material in a volatile non-aqueous solvent in which the first coat is insoluble, then evaporating the non-aqueous solvent from the second coat. Another way of applying the second coat on the first coat is by spraying the first coat with second coat material dissolved in a suitable volatile non-aqueous solvent. A further method of applying a first coat on the electrode body is by electrospinning a viscous solution or suspension of first coat material along the electrode body. The viscous solution is applied onto the electrode body through a nozzle, which preferably is fixed while the electrode body is rotated and displaced in a direction of its central axis. Thereby a helical first coat is formed on the electrode body. After drying a second coat of the invention, for instance Parylene C, is applied on the first coat by dipping or spraying or other suitable means such as those described above. A second flexible polymer coat formed on a helical first coat does share the geometry of the first coat, that is, is helical and functions in the manner of a bellows upon dissolution of the first coat.

According to the present invention is disclosed a method of forming a microelectrode of the invention in situ in soft tissue. The method comprises:

Providing a proto microelectrode comprising a first coat of water dissolvable and/or degradable and/or swellable material on an oblong electrode body comprising or consisting of a metal or a metal alloy or an electrically conducting form of carbon or an electrically conducting polymer or a combination thereof, a second coat of electrically insulating, flexible, optionally resilient water insoluble material on the first coat; inserting the proto microelectrode into soft tissue with its front end foremost; equilibrating the proto microelectrode in the tissue with aqueous body fluid so as to remove the water soluble material by dissolution or degradation and/or make it take up water and swell, thereby providing a column of body fluid disposed between the electrode body and the second coat;

with the proviso that access of body fluid to the water soluble first coat is provided at or near the front end of the proto microelectrode through one or more through openings in the second coat.

According to the present invention is disclosed the use of the microelectrode of the invention and the proto microelectrode of the invention for providing electrical stimulation to structures of soft tissue such as neurons, for recording electrical signals emanating from such structures, and for combined drug delivery, recording of nerve cell signals and nerve cell stimulation. Stimulation frequencies up to 100 Hz but even up to 500 Hz are preferred, as well as pulse lengths from 0.05 ms to 2 ms. Preferred pulse voltages are up to 10 V, in particular up to 2 V.

According to a variation of the invention is disclosed a proto semiconductor element from which a semiconductor element shielded from tissue is formed in situ upon insertion of the proto semiconductor element into soft tissue, comprising or substantially consisting of a semiconductor body having a front (distal) end and a rear (proximal) end, a first coat of a water soluble and/or swellable and/or degradable material on the semiconductor body extending along the body at least over a portion extending from its front end towards its rear end, and a second coat of water insoluble flexible polymer material on the first coat, the second coat comprising one or more through openings at or near its front end. In the proto semiconductor element the material of the first coat is one readily soluble in aqueous body fluid, for instance glucose, or is one which is not readily soluble in aqueous body fluid, for instance glucose acetate, or one of intermediate solubility, such as partially acetylated glucose. Upon inserting the proto semiconductor element into soft tissue the first coat is dissolved or swells or is degraded, so as to form a semiconductor element shielded from tissue by body fluid disposed in the space between the semiconductor element and the second coat. The materials of the first and second coat of the proto semiconductor element of the invention are preferably of same kind as those of the first and second coat of the proto microelectrode of the invention. The (proto) semiconductor body can be electrically connected with a control unit by electrically conducting, insulated metal wire(s) extending from a distal end portion thereof. The semiconductor body can be provided, for instance, with a vibrator rod or an optical fiber or an LED for light stimulation.

The invention will now be explained in greater detail by reference to a number of preferred embodiments illustrated in a rough drawing, in which the width of single electrodes/proto electrodes or electrode prestages is generally exaggerated for reasons of clarity.

DESCRIPTION OF THE FIGURES

All Figures illustrate embodiments of the invention. It is shown in

FIG. 5a the front portion of a proto electrode corresponding to a fifth embodiment of the electrode of the invention, an axial section F-F;

FIG. 5b a modification of the front portion of FIG. 5a, in an axial section G-G;

FIG. 5c the front portion of a fifth embodiment of the electrode of the invention, in an axial section H-H;

FIG. 9 the front portion of a proto electrode corresponding to a ninth embodiment of the electrode of the invention, in an axial section M-M;

FIGS. 10a, 10b the front portions of a proto electrode corresponding to a tenth embodiment of the electrode of the invention and of the corresponding electrode of the invention, in axial sections N-N;

FIGS. 11a-11c a proto electrode bundle comprising four electrodes of the invention, in a longitudinal section R-R (8a), and two radial sections O-O and P-P (8b, 8c);

FIGS. 12a, 12b a modification of the proto electrode bundle of FIGS. 11a-11c, embedded in a water soluble first coat of the same kind as that of the proto electrode first coat, in a longitudinal section S-S (12a) and a radial section T-T (12b);

FIGS. 13a, 13b a proto electrode array comprising six proto electrode bundles of the invention, in a sectional view V (13a) and a partial side view (13b, seen in Z direction);

FIG. 14 an electrode array comprising nine electrode groups each consisting of five electrodes, in an angular side view;

FIG. 15 a further embodiment of the proto electrode of the invention, comprising a semiconductor element, in the same view as the electrode of FIG. 3;

FIG. 16 an implantable thermally shielded semiconductor proto element for non-electrode applications, in the same view as the electrode of FIG. 3;

FIG. 17a a prestage electrode of the invention, corresponding to eleventh and twelfth embodiments of the electrode of the invention, in the same view as FIG. 1a;

FIG. 17b a proto electrode corresponding to an eleventh embodiment of the electrode of the invention produced from the prestage electrode of FIG. 17a and in the same view;

FIG. 17c a first stage of a proto electrode corresponding to a twelfth embodiment of the electrode of the invention produced from the prestage electrode of FIG. 17a and in the same view;

FIG. 19a a further embodiment of a prestage electrode of the invention corresponding to an electrode in which the electrode body is somewhat withdrawn into a bellows-formed second coat, in the same view as in FIG. 17d;

FIG. 19b a proto electrode of the invention formed from the prestage electrode of FIG. 19 a and in the same view.

DESCRIPTION OF PREFERRED EMBODIMENTS

In the examples, either a proto electrode of the invention and/or the corresponding electrode of the invention are shown. In Example 1 a corresponding prestage of the proto electrode is shown, from which the latter is manufactured. Reference numbers are the same for functionally corresponding elements of an electrode and the electrode prestage and proto electrode thereof. The same numbers are retained for functionally similar elements of proto electrodes and electrodes pertaining to different embodiments of which each is identified by preceding digit(s).

EXAMPLE 1

Figure 1:
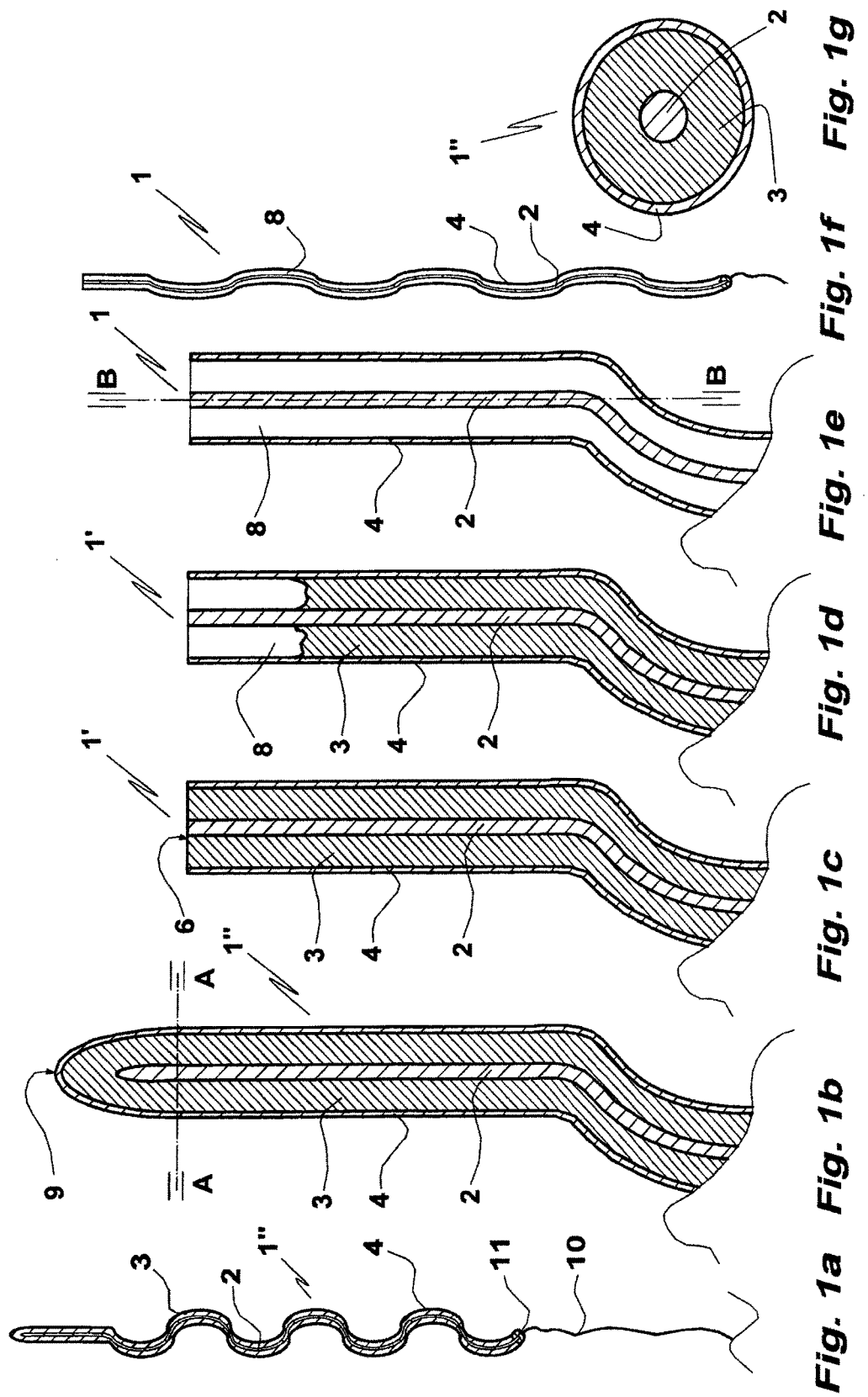
FIG. 1a an electrode prestage of a first embodiment of the electrode of the invention, in a longitudinal axial section corresponding to axial section B-B in FIG. 1e.
FIG. 1b the front portion of FIG. 1a, in the same view.
FIG. 1c the front portion of a proto electrode of a first embodiment of the electrode of the invention manufactured from the electrode prestage of FIGS. 1a, 1b, in the same view.
FIG. 1d the front portion of FIG. 1c upon insertion into soft tissue and partial dissolution of its water soluble first coat, in the same view.
FIGS. 1e, 1f, the front portion of a first embodiment of the electrode of the invention (FIG. 1e) and the complete embodiment in a longitudinal extended state (FIG. 1f), in a longitudinal axial section B-B.
FIG. 1g a radial section A-A of the electrode prestage of FIG. 1b, in the same view.
Figure 2:
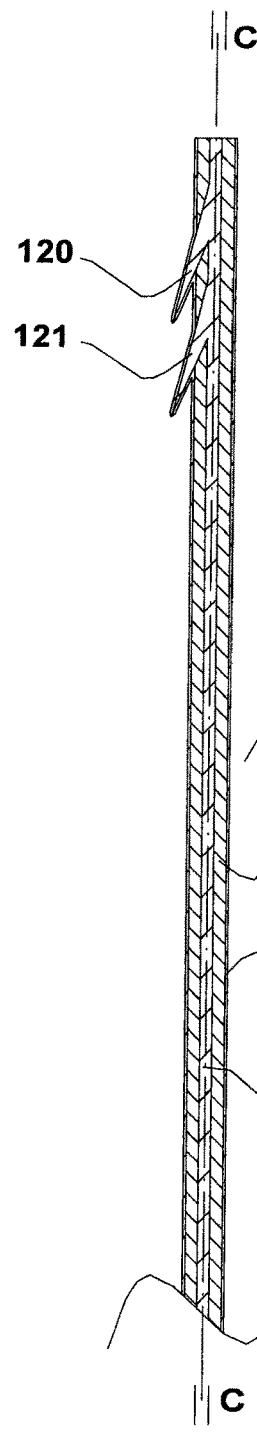
FIG. 2 the front portion of a proto electrode corresponding to a second embodiment of the electrode of the invention, in an axial section C-C.

First Embodiment of the Electrode of the Invention and Corresponding Prestage and Proto Electrodes The first embodiment of the proto electrode of the invention of FIG. 1c is manufactured from an electrode prestage 1" illustrated in FIGS. 1a, 1b. The electrode prestage 1" is made by coating an oblong metal electrode body 2, in particular a thin metal wire 2, coated with a water dissolvable or water degradable material to form a first coat 3, and further coating the first coat 3 with a flexible polymer material to form a second coat 4. The electrode prestage 1" has a blunt front end 9 and a rear end 11 at an electrically insulated conductor 10 soldered to it. The electrode prestage 1" is oblong and comprises, except for a cylinder section (central axis B-B only shown in FIG. 1e) extending from its front end 9, a number of sections curved forth and back. The curvatures allow the electrode 1 of the invention derived from it to extend and shrink in a longitudinal direction so as to follow the movements of surrounding tissue. By radial cutting near its front end 9 (radial section A-A) the electrode prestage 1" is transformed to the proto electrode 1' (FIG. 1c). The proto electrode 1' has a flat end face 6 at which its electrode body 2 and water dissolvable coat 3 are not shielded electrically and from the action of aqueous fluid. Upon insertion of the proto electrode 1' into soft tissue with its front end foremost contact is made with aqueous body fluid. The body fluid starts to dissolve the water soluble coat 3, which is transported away from the front end of the proto electrode 1' by diffusion and convection (FIG. 1d). Thereby a space 8 is being formed between the electrode body 2 and the second coat 4 filled with body fluid and dissolved first coat material. After a period of time depending, i. a., on the nature of the water dissolvable coat and the dimensions of the proto electrode 1' the entire first coat 3 has been dissolved and the electrode 1 of the invention formed (FIGS. 1e, 1f). The material of the first coat can be one which is readily soluble in aqueous body fluid, such as glucose, or one which is not readily soluble in aqueous body fluid, such as glucose acetate, or one of intermediate solubility, such as partially acetylated glucose. A material of first coat of a desired dissolution rate can be obtained by combining materials of differing solubility and/or dissolution properties like glucose and gelatin. The electrode 1 of the invention comprises an electrode body 2 surrounded by a flexible, electrically insulating polymer coat 4 interspaced by a void 8 filled with body fluid. A radial section A-A of the first embodiment of the proto electrode 1" of the invention 1 is illustrated in FIG. 1g. FIGS. 1a through 1g are rough presentations and not to scale. FIGS. 1b through 1e and 1g are enlarged in respect of FIGS. 1a, 1f.

EXAMPLE 2

Second Embodiment of the Electrode of the Invention Illustrated by its Proto Electrode The front portion of a proto electrode 101' corresponding to a second embodiment of the electrode of the invention comprises, in addition to an electrode body 102 coated with a water dissolvable material forming a first coat 103, a second flexible coat 104 of water insoluble, electrically insulating polymer material on the first coat 103. The front portion of the proto electrode 101'differs from the front portion of the proto electrode 1' by the provision of two hooks 120, 121 extending from the electrode body 102 in rearward direction with an angle of about 15°. The hooks 120, 121 are provided for anchoring the electrode of the invention obtained on insertion of the proto electrode 101' into soft tissue and dissolution of the first coat 103 in the tissue. Except for the hooks 120, 121 the front portion of the proto electrode 101' is rotationally symmetric about a central axis C-C. In this embodiment the hooks are covered by the second flexible coat; they may, however, also be free from this coat at their points.

EXAMPLE 3

Third Embodiment of the Electrode of the Invention Illustrated by its Proto Electrode The proto electrode 201' is rotationally symmetric in respect of a central longitudinal axis D-D and corresponds to a third embodiment of the electrode of the invention. The proto electrode 201' comprises, in addition to an electrode body 202 coated with a water dissolvable material forming a first coat 203, a second coat 204 of a flexible, water insoluble polymer material. The proto electrode 201' differs in respect of its front portion from the proto electrode 1' by the provision of a rounded cap 207 on its front end. The purpose of the cap 207 is to minimize tissue damage caused by inserting the proto electrode 201' into soft tissue. The material of the cap 207 is one that is readily dissolvable in body fluid but different from water soluble material of the first coat 203. At the proximal end of the proto electrode body 202 an insulated flexible metal wire 210 is attached by a solder 211 to the body 202.

EXAMPLE 4

Figure 3:
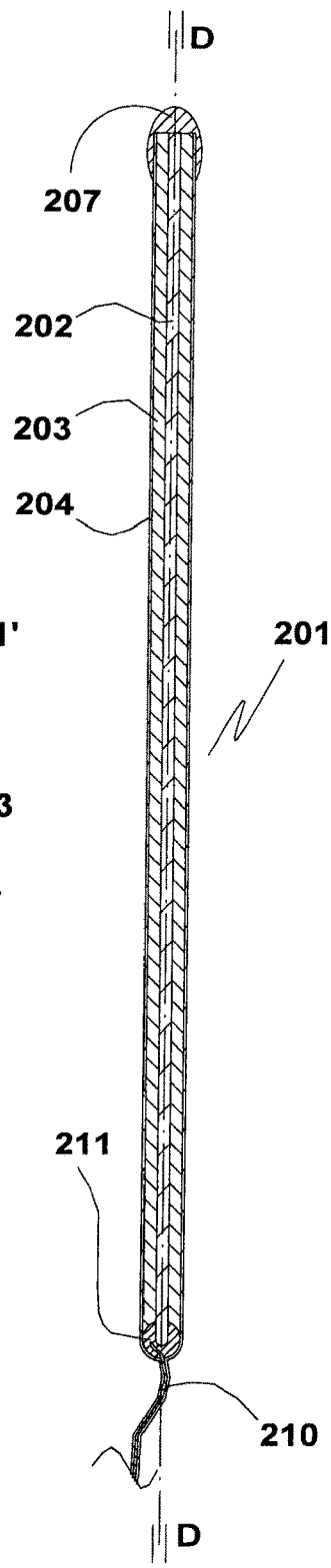
FIG. 3 a proto electrode corresponding to a third embodiment of the electrode of the invention, in an axial section D-D.
Figure 4:
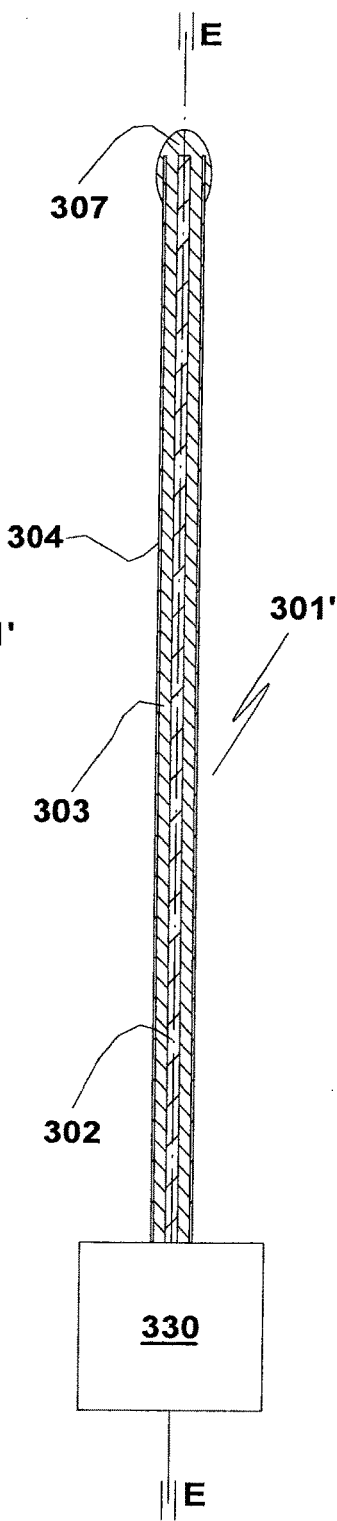
FIG. 4 a proto electrode corresponding to a fourth embodiment of the electrode of the invention, in an axial section E-E.
Figure 8:
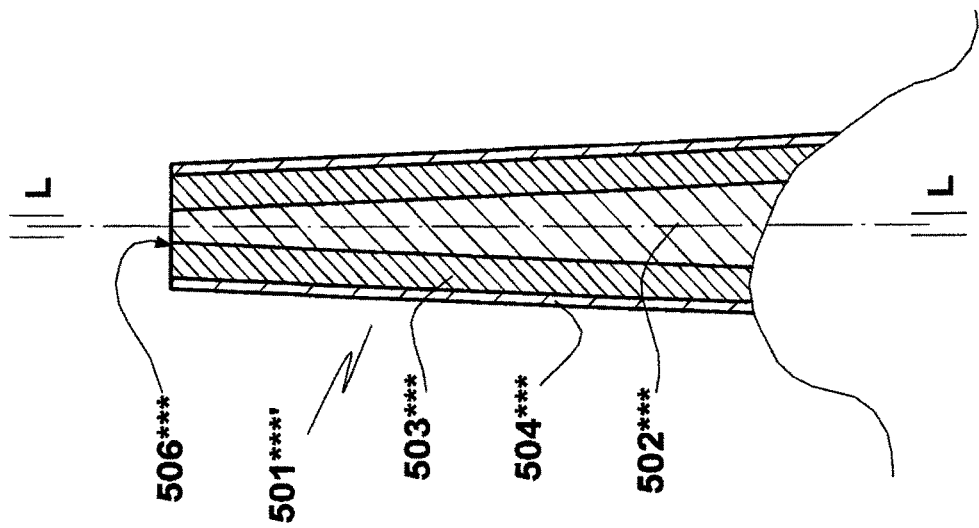
FIG. 8 the front portion of a proto electrode corresponding to an eight embodiment of the electrode of the invention, in an axial section L-L.

Forth Embodiment of the Electrode of the Invention Illustrated by its Proto Electrode The proto electrode 301' is rotationally symmetric in respect of a central longitudinal axis E-E and corresponds to a fourth embodiment of the electrode of the invention. The proto electrode 301' comprises, in addition to an electrode body 302 coated with a water soluble material forming a first coat 303, a flexible second coat 304 of water insoluble polymer material. Its front portion differs from the front portion of the proto electrode 1' by the provision of a rounded cap 307 on its front end of same function as the cap 207 of the embodiment of FIG. 3, but consisting of the same material as the water dissolvable coat 303. At its rear end the proto electrode 301' is connected with a control unit 330, which can be of various kinds and for various purposes, such as for controlling the current and voltage of power fed to the electrode and/or recording and/or transmitting electric signals received from the electrode.

EXAMPLE 5

Fifth Embodiment of the Electrode of the Invention and Corresponding Proto Electrode and Variation Thereof The fifth embodiment 401 of the electrode of the invention illustrated in FIG. 5c by means of a front section thereof is rotationally symmetric about a central longitudinal axis H-H and comprises a metallic electrode body 402 and a second coat 404 of polymer, water insoluble material disposed radially distant from the body 402 so as to provide a tubular space 408 filled with body fluid. Except for lateral openings 413, 414 the second coat 404 is intact. The electrode of the invention is formed by insertion of a corresponding proto electrode 401 (rotationally symmetric about longitudinal axis F-F into soft tissue, manufactured from an electrode prestage (not shown) by removing by, for instance, abrasion portions of the second coat 404 (FIG. 5a) and covering the so formed openings 413, 414 that provide access to a first coat 403 of water soluble material with a cap 407 (longitudinal axis G-G). The cap 407 is of a water soluble material and has the same function as the cap 207 of FIG. 3.

EXAMPLE 6

Figure 6:
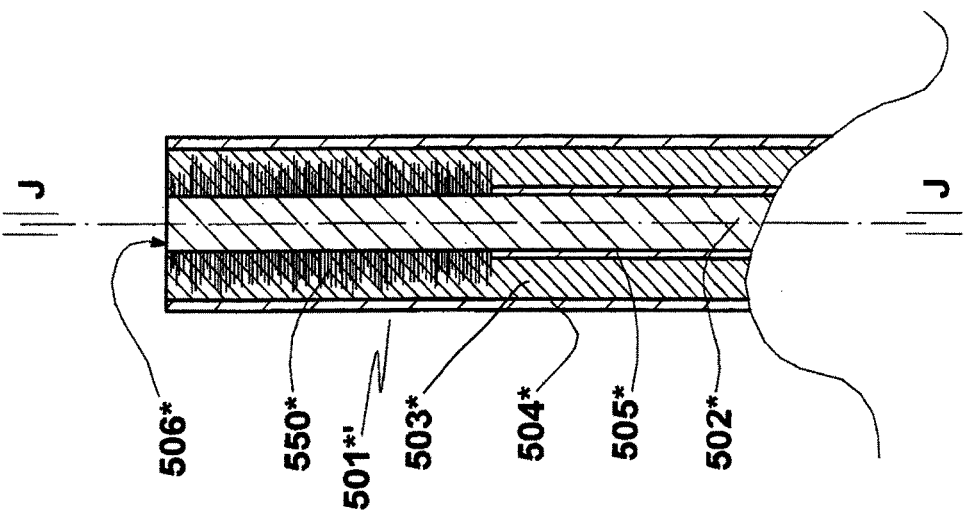
FIG. 6 the front portion of a proto electrode corresponding to a sixth embodiment of the electrode of the invention, in an axial section J-J.

Sixth Embodiment of the Electrode of the Invention Illustrated by a Front Portion of its Proto Electrode The cylindrical (central axis J-J) proto electrode **501\*' of the invention illustrated in FIG. 6 has a flat frontal face 506\* and comprises an electrode body 502\*. A terminal section of the electrode body 502\* extending from the front end is provided with a brush 550\* of tiny metallic fibers, which extend radially from the body 502\* to provide for a large electrode surface. Proximally of the brush 550\* the electrode body 502\* is electrically insulated by a thin polymer coat 505\*. The electrode body 502\* is enclosed in a first coat 503\* of water soluble material on which a second coat 504\*** of water insoluble polymer material is provided.

EXAMPLE 7

Figure 7:
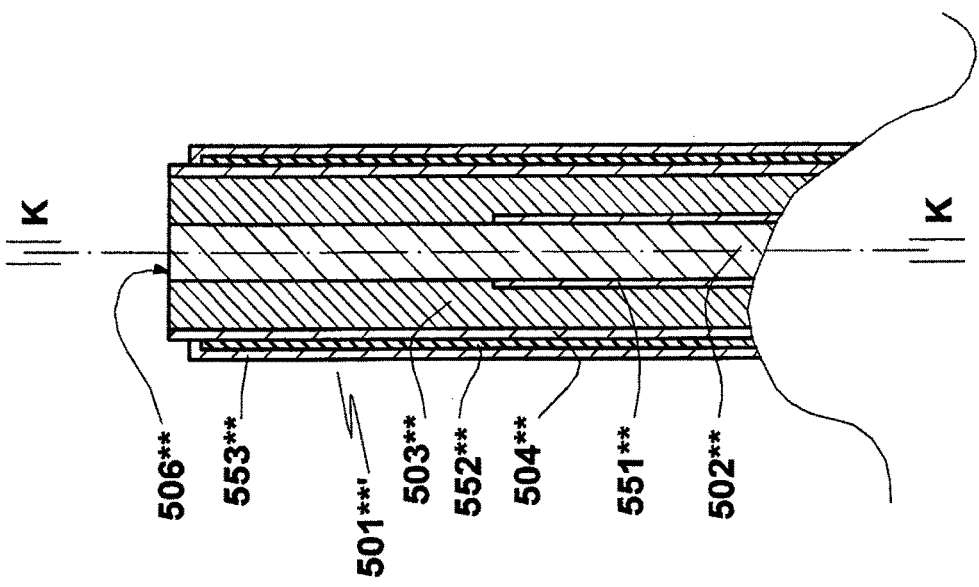
FIG. 7 the front portion of a proto electrode corresponding to a seventh embodiment of the electrode of the invention, in an axial section K-K.

Seventh Embodiment of the Electrode of the Invention Illustrated by a Front Portion of its Proto Electrode The cylindrical (central axis K-K) proto electrode **501\*\*' of the invention illustrated in FIG. 7 has a flat frontal face 506\*\* and comprises an electrode body 502\*\*, which is electrically insulated by a thin polymer first layer 551\*\* applied over its entire length starting at a short distance from the front face 506\*\* of the proto electrode 501\*\*'. The electrode body 502\*\* is enclosed in a first coat 503\*\* of water soluble material on which a second coat 504\*\* of water insoluble polymer material is provided. A thin layer of gold 552\*\* has been deposited on the second coat 504\*\* by ion sputtering. The gold layer 552\*\*, which extends almost to the front end of the electrode, is electrically insulated over its entire length by a second layer 553\*\* of same polymer material as the second coat 504\*\*. The gold layer 552\*\* is at earth potential and arranged for electrically shielding the electrode body 502\*\*** except at the front end thereof.

EXAMPLE 8

Eight Embodiment of the Electrode of the Invention Illustrated by a Front Portion of its Proto Electrode The proto electrode **501\*\*\*' of the invention has a flat frontal face 506\*\*\* and comprises an electrode body 502\*\*\* having the form of a frustrum of a cone (cone axis L-L). The electrode body 502\*\*\* is enclosed in a first coat 503\*\*\* of water soluble material on which a second coat 504\*\*\*** of water insoluble polymer material is provided.

EXAMPLE 9

Ninth Embodiment of the Electrode of the Invention Illustrated by a Front Portion of its Proto Electrode The proto electrode 601' of cylindrical form (central axis M-M) of the invention of FIG. 9 is similar to that of FIG. 5a except for the soluble material of the first coat consisting of two sections, a frontal (distal) section 603 and a proximal section 603' extending rearwards from the distal end of the frontal section 603. Elements 602, 604, 613, 614 correspond functionally to elements 402, 404, 413, 414 of the embodiment of FIGS. 5a, 5b. The purpose with providing two or more water soluble first coat sections joining each other in radial plane(s) will be explained further down.

EXAMPLE 10

Tenth Embodiment of the Electrode of the Invention and Corresponding Proto Electrode The tenth embodiment of the proto electrode of the invention 701' of FIG. 10a (axial section N-N) comprises a front portion functionally similar to that of the embodiment of FIG. 9, elements 702, 703, 704, 713, and 714 corresponding to elements 602, 603, 604, 613, and 614, respectively. The water soluble material of the first coat 703 does not extend along the entire electrode body 702 but only over a portion thereof extending rearwards from the electrode front end. At the rear end of the first coat 703 a bulged container 715 of polymer material through which the electrode body 702 extends centrally is joined to the proto electrode 701'. The rear end of the container 715 is joined to a stiff polymer tube 717 through with the electrode body 702 further extends. The stiff tube 717 is so dimensioned that a tubular void 718 is formed between it and the container 715. The container 715 is filled with a porous, water insoluble material 716, for instance silica. A pharmacologically active compound, such as dopamine, is adsorbed on the porous material 716. By dissolution of the water soluble first coat 703 by aqueous body fluid entering through openings 713, 714 the void between the electrode body 702 and the second coat 704 of water insoluble polymer material becomes filled with body fluid.

By this process the proto electrode of FIG. 10a is transformed to the corresponding electrode 701 of the invention (FIG. 10b). By provision of a controlled forward flow F of saline in the void 718 of tube 717 dopamine adsorbed on the porous material 716 is dissolved and carried away into the void 708 and, from there, through the openings 713, 714 into adjoining tissue to exert its effect on neurons, the electrical activity of which can be monitored by the electrode 701.

EXAMPLE 11

Embodiment of a Proto Electrode Bundle of the Invention

The proto electrode bundle 800' of the invention illustrated in FIGS. 11a (section R-R), 11b (section O-O) and 11c (section P-P) comprises four proto electrodes 801a', 801b', 801c', and 801d' of the invention disposed in parallel and mounted in through bores of a cylindrical base 820. Each of the proto electrodes 801a', 801b', 801c', 801d' comprises a central electrode body 802a, 802b, 802c, and 802d, respectively, a water soluble first coat 803a, 803b, 803c, and 803d, respectively, on the corresponding electrode body, and a water-insoluble polymer second coat 804a, 804b, 804c, and 804d, respectively, on the corresponding first coat. The proto electrodes 801a', 801b', 801c', 801d' are arranged symmetrically in respect of a central electrode bundle axis Q-Q. The electrode bodies 802a, 802b, 802c, 802d are integral with insulated electrical conductors of which only insulated 822a, 822c conductors 810a, 810c are shown. The conductors, such as conductors 810a, 810c, connect the respective electrode body 802a, 802c with an electrode bundle control unit (not shown). Each of the various proto electrodes of the invention described in the preceding embodiments, as well as the embodiments illustrated in FIGS. 17b-d and FIGS. 18a, 18b can be bundled to form a proto electrode bundle of the invention or incorporated into an array of the invention as such or bundled. A proto electrode bundle of the invention can comprise two or more different proto electrodes of the invention. By insertion of a proto electrode bundle of the invention into soft tissue a corresponding electrode bundle of the invention is formed by dissolution of the water soluble matrices of its constituent electrodes. The proto electrode bundle of the invention can also be formed from two or more electrodes of the invention by gluing them together using a glue which is water dissolvable or degradable or one which is not.

To facilitate insertion into soft tissue, the proto electrode bundle of the invention is incorporated into a shell 880 of a water soluble material, as shown in FIGS. 12a (section T-T) and 12b (section S-S) for the electrode bundle of FIGS. 11a-11c. In FIGS. 12a, 12b the reference numbers of FIGS. 11a-11c are retained. The shell 880 has a blunt front end, is rotationally symmetric about the bundle axis Q, and extends to the base 820.

After insertion into soft tissue, the proto electrode bundle of FIGS. 11a-11c or FIGS. 12a, 12b is transformed to a corresponding electrode bundle of the invention by dissolution of its layers/coats of water soluble material, including its shell, if any.

EXAMPLE 12

Embodiment of a Proto Electrode Bundle Array of the Invention

The proto electrode array of the invention shown in FIG. 13a (section V-V) comprises six proto electrode bundles 901', 902', 903', 904', 905', 906' each comprising pairs of proto electrodes of the invention of the same kind as the proto electrodes of the proto electrode bundle 800' of FIGS. 11a-11c. Each of the proto electrode bundles 900a', 900b', 900c', 900d', 900e', 900f' is mounted at its rear end in a bundling holder, only the holder 911a for bundle 900a' being specifically identified in FIGS. 13a. 13b. The bundling holders 911a are mounted by gluing on an oblong, about rectangular flat base 910 with a pointed front end 909. The base is preferably of a biocompatible polymer material like polypropylene, polyacrylate or polycarbonate. Holder 911a and the other holders are mounted symmetrically in respect of the long base axis U-U so that three of the proto electrode bundles 900a', 900b', 900c' are mounted at the left hand long edge 970 of the base 910 and the other three 900d', 900e', 900f' at the right hand long edge 971 of the base 910, in a manner so as to have front end portions of the proto electrode bundles 900a', 900b', 900c', 900d', 900e', 900f' extend over the respective edge in oblique forward directions. Near the rear end of the base 910 the leads of the left hand 900a', 900b', 900c', and right hand 900d', 900e', 900f' proto electrode bundles are combined in polymer tubes 907, 908. To facilitate insertion into soft tissue, each of the proto electrode bundles and/or, in particular, the proto electrode bundle array can be incorporated in a shell of a water soluble material, as shown for the proto electrode bundle 801' in FIGS. 12a, 12b. After insertion into soft tissue, the proto electrode bundle array of FIGS. 13a, 13b is transformed to a corresponding electrode bundle array of the invention by dissolution of its layers of water soluble coat material, including its shell, if any.

EXAMPLE 13

Electrode Array

The electrode array 1001 of FIG. 14 comprises a thin circular flat support of polyurethane 1002 from one (top) face of which nine groups of electrodes of equal length 1003, 1004, 1005, 1006, 1007, etc. of the invention extend perpendicularly from said face so as to be disposed in parallel in respect to each other. Each group comprises five electrodes of the invention. The electrodes of groups 1003, 1004, 1005, 1006, 1007, etc. penetrate the support 1002 and extend for a short distance from its other (bottom) face. Their rear ends are connected by thin insulated gold wires bundled in a flexible tube 1008 with a control unit 1009. The control unit 1009 allows a person energize selected groups of electrode and even selected electrodes within one group. This allows a desired energizing pattern to be created. Alternatively the control unit allows monitoring the voltage at individual electrodes in a group and/or at selected groups of electrodes in respect to earth or other reference potential.

EXAMPLE 14

Coating an Electrode Body with Water Soluble Material

Electrode body of stainless steel; length 10 mm, diameter 12 μm. Grease and oil is removed by dipping the body into diethyl ether for 10 second, removing it and drying. A sugar coating of about 30 μm thickness is applied to the body in the following manner. Sucrose (100 g) is dissolved in 50 ml water. The solution is boiled for about 5 min until it appears clear. The solution is allowed to cool to 80° C. The electrode body held at its rear end by a pair of stainless steel pincers is dipped fully into the solution. It is removed from the solution by withdrawing it vertically with a speed of 6 mm/s. The sucrose coated electrode body is dried overnight so as to form a dry sucrose coat on the body of about 40 µm thickness. The thickness of the coat can selected by varying the speed of withdrawal. Lowering the speed renders a thinner coat.

EXAMPLE 15

Manufacture of an Electrode Prestage of the Invention by Coating the Dry Sucrose Coated Electrode Body of Example 14 with Parylene C A coat of Parylene C of about about 4 µm thickness is applied by a state-of-the-art vacuum coating process (http://www.scscookson.com/parylene/properties.cfm) in which di-para-xylylene is vaporized and then pyrolized to paraxylylene, which is adduced under high vacuum to a deposition chamber kept at about room temperature and there deposited on the sucrose coated electrode body. The twice coated electrode body thus obtained corresponds to an electrode prestage of the invention.

EXAMPLE 16

Manufacture of a Proto Electrode of the Invention from the Electrode Prestage of Example 15

The electrode prestage of Example 15 is dipped with its front end foremost into molten high melting paraffin (m.p. of about 40° C.) in a short a 3 mm diameter polypropylene cylinder. After cooling to room temperature, the paraffin block containing the electrode prestage is put a polypropylene support and cut radially with a razor blade so as to sever the electrode tip. After removing most of the paraffin by melting the block and withdrawing the proto electrode the latter is rinsed several times with pentane, and dried. The recorded impedance of the insulated electrode body prior to cutting is >10 megohm, measured with the electrode body immersed into saline. The recorded impedance after cutting the tip and immersion of the electrode body into saline for 2-3 hours is <50 kohm. Alternatively, the electrode prestage of Example 15 is fixed under a microscope and portions of the Parylene C coat near the front end are removed by scraping the coat with a micro file made by coating a thin steel wire (0.1 mm diameter) with titanium oxide powder (grain of about 10 µm) by means of cyanoacrylate prepolymer dissolved in diethyl ether, into which the wire is dipped immediately prior to the application of the powder. Alternatively, when small openings are desired, laser milling the second coat can be used to provide them. Dimensions of the electrode body can vary within a broad range: diameters of up to 100 µm or more are useful. A preferred diameter is from 5 µm-30 µm. The diameter of the electrode body can vary along the body length. For example, the diameter can be about 50 µm at the proximal end and 5 µm at the distal end. The length of the electrode body can be adapted to the desired location of the electrode after insertion.

EXAMPLE 17

Electrode of the Invention Comprising a Semiconductor Element

Figure 15A:
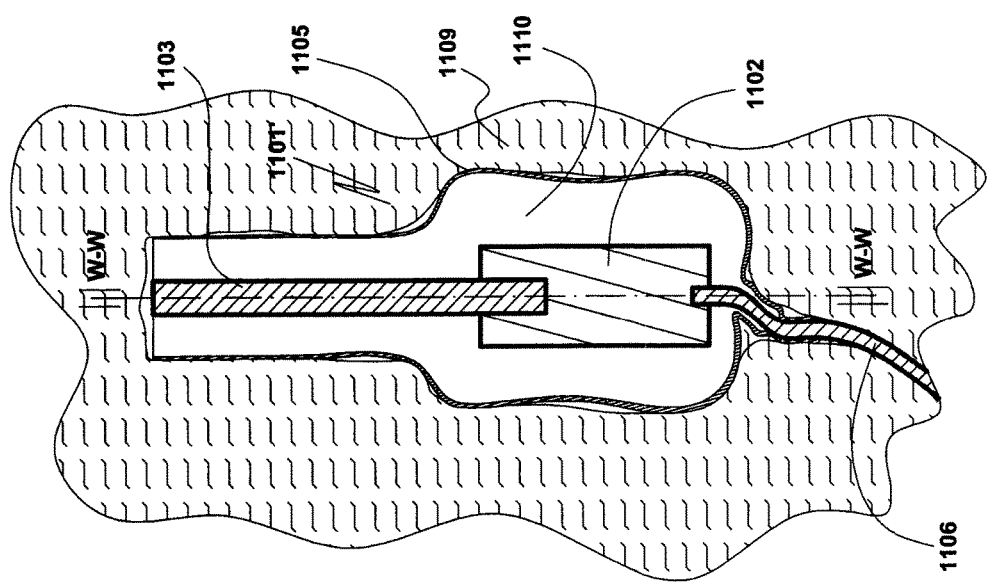
FIG. 15a an electrode of the invention corresponding to the proto electrode of FIG. 15, in the same view.

As shown in FIG. 15 the proto electrode 1101 of the invention, which is about rotationally symmetric in respect to a central axis W-W, can be provided with a semiconductor element 1102 such as, for instance, an amplifier circuit. In a working (amplifying, etc.) state, that is upon insertion of the proto electrode into soft tissue 1109 and equilibration with aqueous body fluid 1110 so as to transform the proto electrode 1101 to the corresponding electrode 1101' of the invention shown in FIG. 15a, the temperature of the powered semiconductor element 1102 can rise, possibly to a tissue damaging level. For this reason, the semiconductor element 1102 is shielded from direct contact with tissue in the same manner as the electrode body 1103, that is, by a zone of tissue fluid 1110 disposed between the semiconductor element 1102 and a coat corresponding to and integral with the second, electrically insulating and flexible polymer electrode coat 1105. As with other electrodes of the invention the zone of tissue fluid 1110 is created in the same manner as with electrodes of the invention lacking a semiconductor element, that is, by dissolution in or swelling by a proto electrode first coat 1104 of water soluble material such as sucrose or a water swellable material such as gelatin, which first coat 1104 is shared by the electrode body 1103 and the semiconductor element 1102. The semiconductor element 1102 is preferably arranged at the proximal end of the proto electrode body 1103, and thus at the proximal end of the proto electrode 1101. The semiconductor element 1102 is electrically connected by insulated metal wires (1106, only one shown) to an electrode control unit (not shown), which may be one implanted in the patient or be extracorporeal. Reference no. 1107 identifies the front or distal face of the proto electrode 1101 at which the first coat 1104 is not protected by the flexible polymer second coat 1105 and thus is contacted by body fluid upon insertion into soft tissue to be dissolved in or swollen by body fluid. For ease of insertion into soft tissue 1110, the proto electrode 1101 is provided with a rounded cap 1108 attached to its distal face 1107. The cap 1108 is of a biocompatible material dissolvable in body fluid 1109, in particular of a low molecular weight carbohydrate such as sucrose. To protect the cap 1108 from premature dissolution is can be provided with a thin coat of a dissolution delaying material, for instance kollicoat. The material of the cap 1108 can be different from the material of the first coat 1104, which is the alternative shown in FIG. 15, or of the same material.

EXAMPLE 18

Figure 16A:
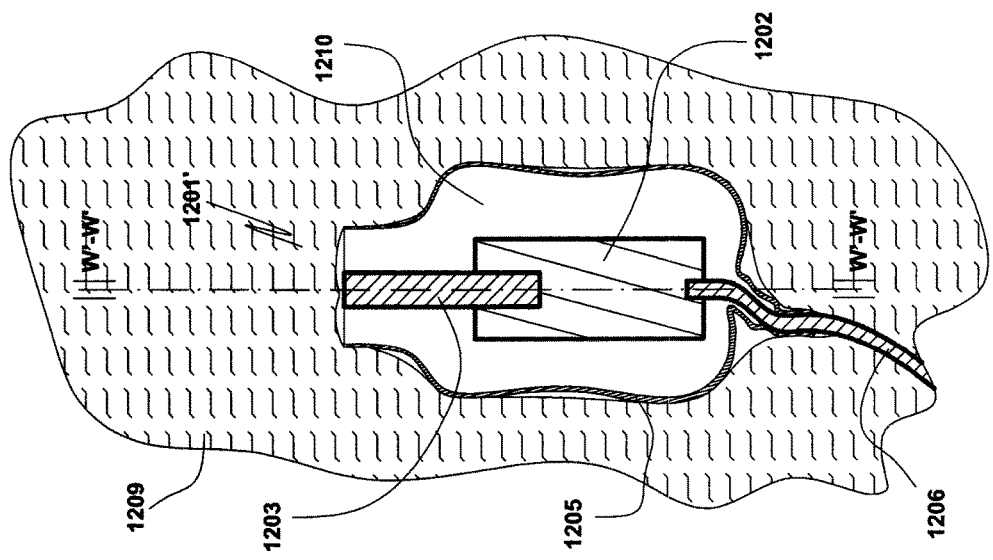
FIG. 16a a shielded semiconductor element corresponding to the proto element of FIG. 16, in the same view.

Implantable Thermally Shielded Semiconductor Element for Non-electrode Applications For certain applications the embodiment of the proto electrode 1101 of the invention illustrated in FIG. 15 can be modified by substituting its electrode body 1103 by another kind of element, in particular a signal producing or receiving element, such as a vibrator rod or a glass or polymer optical fiber for directing vibrations or visible or invisible radiation into soft tissue or by an antenna for capturing radio frequency signals. An implantable thermally shielded proto semiconductor element 1202 is shown in FIG. 16. Elements identified by reference nos. 1202, 1204-1207 and W'-W' correspond to elements 1102, 1104-1107 and W-W of FIG. 15, respectively. The electrode body 1203 of the device of FIG. 15 has been substituted by a vibrator rod 1203 or an optical fiber 1203 or an LED 1203 for light stimulation. A cap (not shown) corresponding to cap 1108 in the embodiment of FIG. 15 can be applied on the distal face 1207 of the thermally shielded semiconductor element 1202. The implanted state 1201' of the thermally shielded semiconductor element is shown in FIG. 16a, in which reference numbers 1209 and 1210 signify soft tissue and aqueous body fluid, respectively. The semiconductor element 1202 can be joined with a microelectrode of the invention by, for instance, a glue.

EXAMPLE 19

Figures 17A, 17B, 17C:
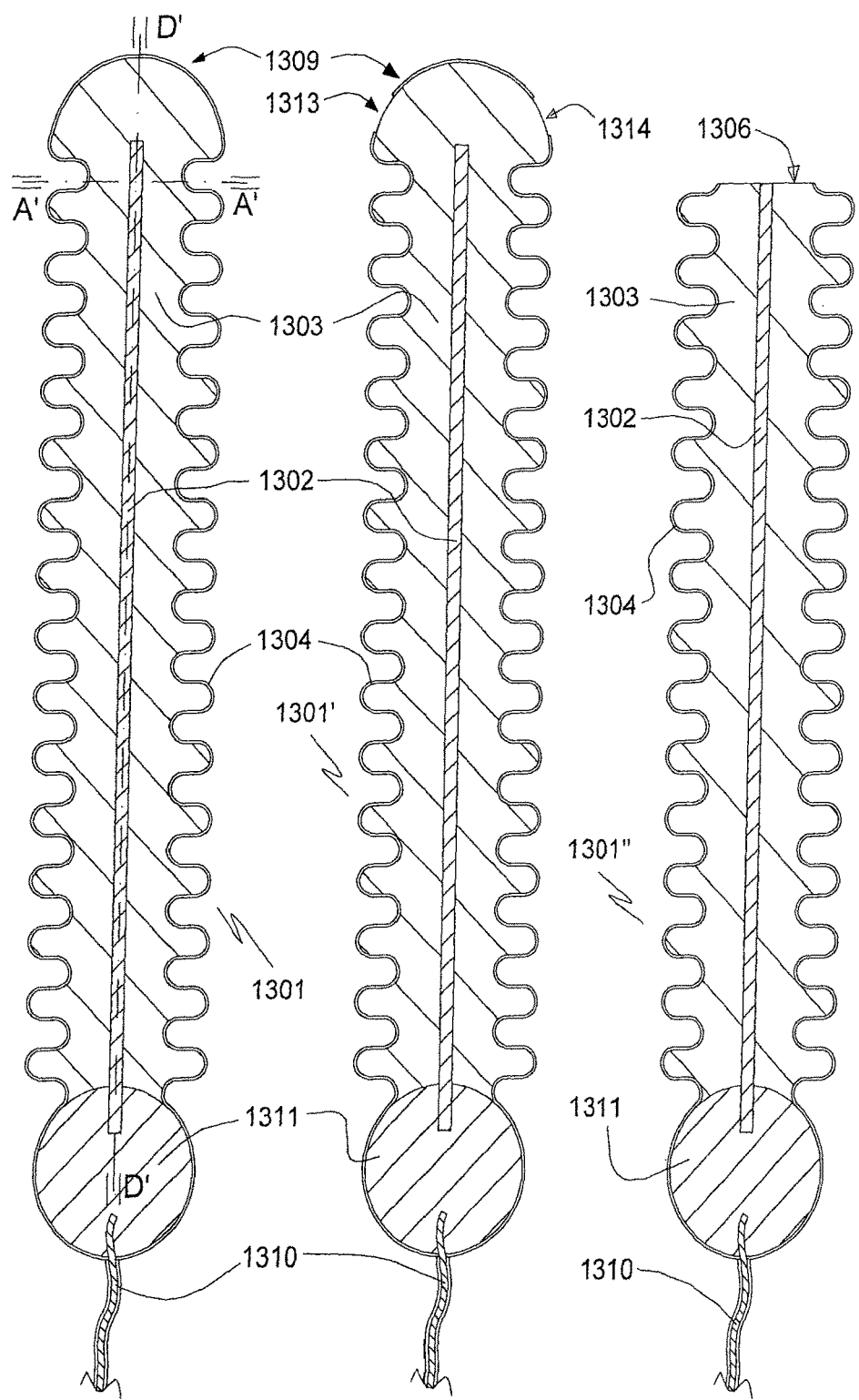

Eleventh and Twelfth Embodiments of the Electrode of the Invention and Corresponding Proto Electrodes The prestage electrode 1301 of FIG. 17a is rotationally symmetric in respect of a central longitudinal axis D'-D'. Eleventh and twelfth embodiments 1301' and 1301" of the proto electrode of the invention can be produced from it. In addition to an electrode body 1302 the prestage electrode 1301 comprises a first rigid coat 1303 of water dissolvable material on an electrode body 1302 and a second thin and flexible coat 1304 of a water insoluble polymer material on the first coat 1303. The second coat 1304 has the form of a bellows tube. At its front end the first coat 1303 enclosing the electrode body 1302 forms a bulge 1309. At the proximal end of the prestage electrode body 1302 an insulated thin and flexible metal 1310 wire is attached to a solder sphere 1311 intermediate between and electrically connecting the wire 1310 and the electrode body 1302 of which a rear end portion is mounted in the solder sphere 1311. A terminal rear portion of the second coat 1304 encloses and insulates the solder sphere 1311. The wire 1310 provides electrical contact with an electrode control unit or similar equipment (not shown), implanted in the body or external of it. The prestage electrode 1301 is transformed into the electrodes of the invention 1301*, 1301** via proto electrodes 1301', 1301".

Proto electrode 1301' corresponding to the eleventh embodiment 1301* of the electrode of the invention. From the second coat 1304 of the prestage electrode 1301 are excised lateral openings 1313, 1314 on the bulge 1309 to expose portions of the first coat 1303 of corresponding form (FIG. 17b). The proto electrode 1301' thus formed is used for implantation.

Figures 17D, 17E, 17F:
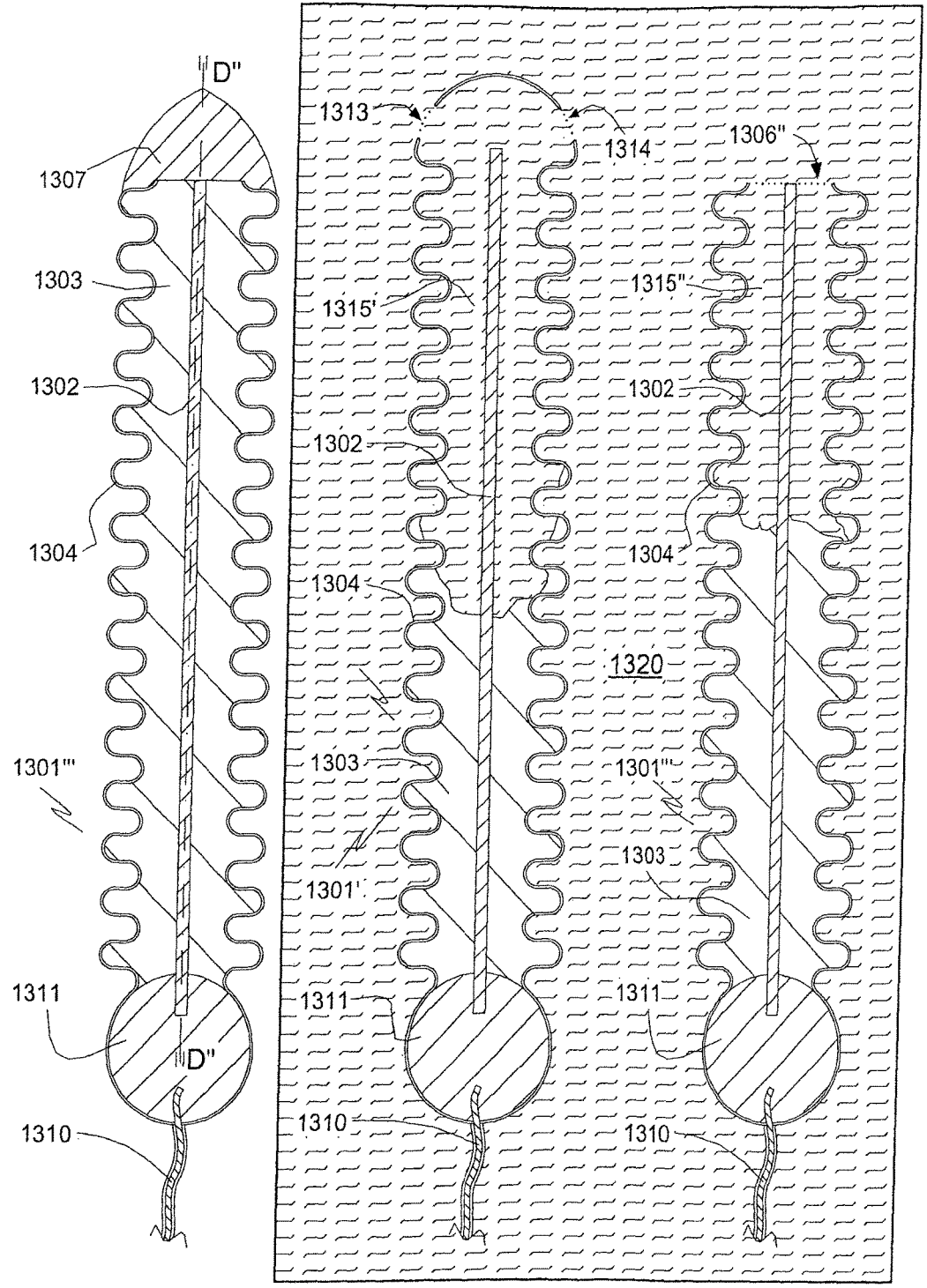
FIG. 17d a proto electrode of the invention produced from the first stage of FIG. 17c and in the same view.
FIG. 17e the proto electrode of FIG. 17b inserted into soft tissue, during its transformation into the eleventh embodiment of the electrode of the invention and in the same view.
FIG. 17f the proto electrode of FIG. 17d inserted into soft tissue, during its transformation into the twelfth embodiment of the electrode of the invention and in the same view.

Proto electrode 1301'" corresponding to the twelfth embodiment 1301** of the electrode of the invention. Near its front end bulge the prestage electrode 1301 is cut in a radial plane A'-A' to form a first stage 1301" of the proto electrode 1301'" (FIG. 17 c). The distally facing cutting face 1306 of the first stage 1301" of the proto electrode 1301'" is then provided with a pointed cap 1307 of water soluble material, either of the same material as that of the first coat or another material of suitable dissolution properties. Thereby the rotationally symmetric (axis D"-D") second stage proto electrode 1301'" is formed (FIG. 17d), which is used for implantation. By providing the pointed cap 1307 tissue damage during insertion of the proto electrode 1301'" into soft tissue is avoided.

Figures 17G, 17H:
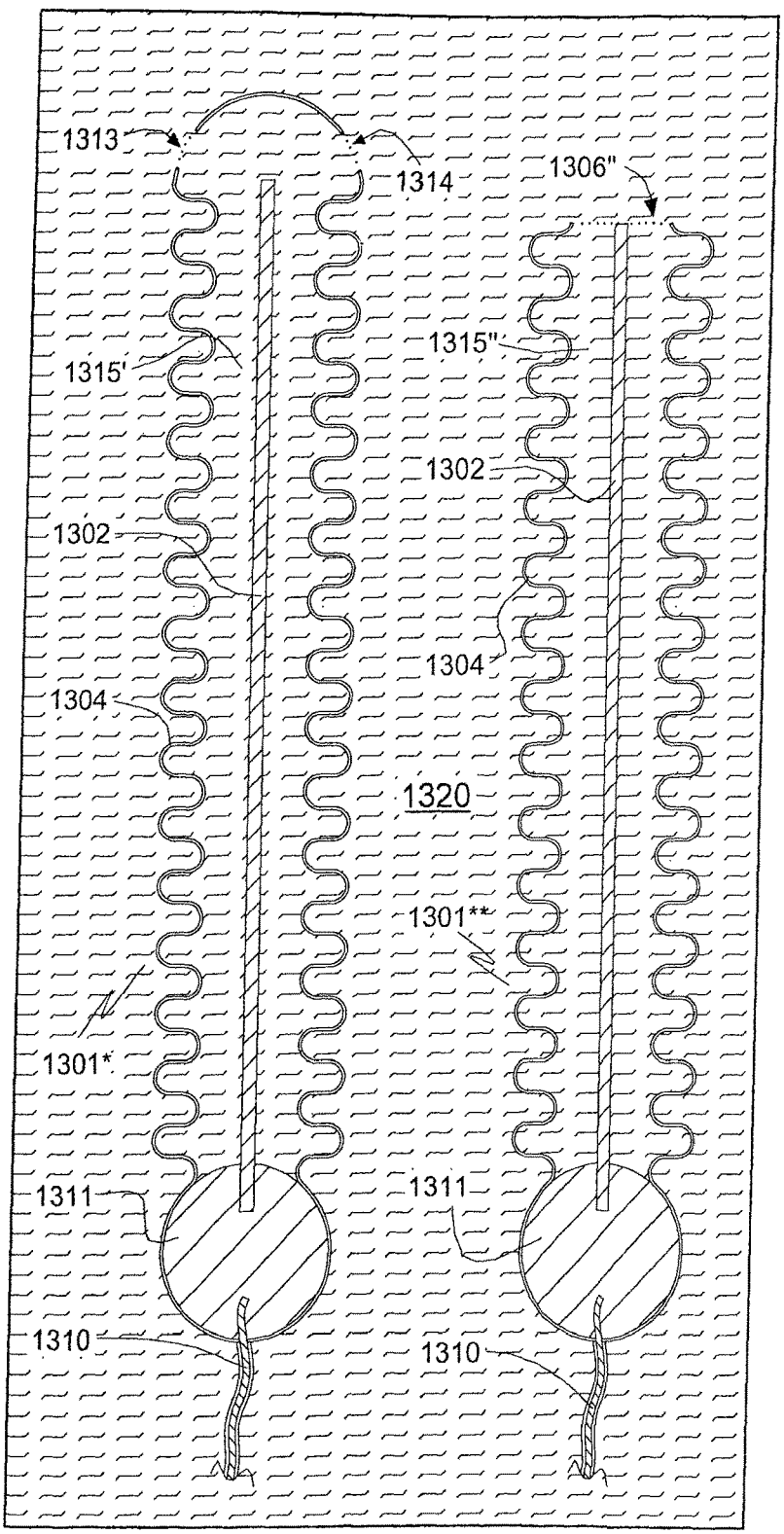
FIG. 17g an eleventh embodiment of the electrode of the invention, formed from the proto electrode of FIG. 17b and in the same view.
FIG. 17h a twelfth embodiment of the electrode of the invention, formed from the proto electrode of FIG. 17d and in the same view.

FIGS. 17e, 17f illustrate the transformation of the proto electrodes 1301', 1301'" inserted into soft tissue 1320 to corresponding electrodes 1301*, 1301** of the invention. by dissolution of their first coats 1303. The dissolution proceeds from the front end of the proto electrodes 1301', 1303'" towards the rear end. The progression rate of the dissolution in the same direction can be controlled by selecting a first coat material possessing suitable dissolution characteristics. By dissolution of first coat 1303 material in body fluid the first coat 1303 disposed between the electrode body 1302 and the second coat 1304 is progressively substituted by aqueous body fluid so that a corresponding void 1315', 1315" filled with body fluid comprising dissolved first coat material is formed. By diffusion and, if the surrounding tissue 1320 is temporarily displaced, by convection, body fluid with dissolved first coat material diffuses out from and/or is expelled from the voids 1315', 1315" and replaced by new body liquid. This process is proceeding until the entire first coat 1303 has been dissolved. The formation of the electrodes of the invention 1301*, 1301** shown in FIGS. 17g, 17h is now complete. It is however not only the electrodes of the invention 1301*, 1301** that are capable of functioning as electrodes but also the proto electrodes 1301', 1301'" as soon a non-insulated area of their electrode body 1302 is contacted by body fluid 1320.

This example is also exemplary for the use of a bellows shaped second coat. The second coat of the prestage or proto electrodes of the invention illustrated in FIGS. 1a-1g, 2, 3, 4, 5a-5c, 6, 7, 8, 9, 10a, 10b, 15, 15a thus can comprise bellows shaped portions which, upon dissolution of the first coat, are transformed in bellows shaped tubes surrounding the electrode body.

Similarly, some or all electrodes and proto electrodes comprised by an electrode bundle of the invention illustrated in FIGS. 11a-11c and 12a, 12b as well as comprised by an electrode array of the invention illustrated in FIGS. 13a, 13b, and 14 can comprise such bellows shaped second coat portions.

Furthermore, the second coat of the implantable thermally shielded semiconductor proto element and of the corresponding shielded semiconductor element of FIGS. 16 and 16a, respectively, can comprise bellows shaped portions.

Further Variations of the Proto Electrode of the Invention

Figure 18A:
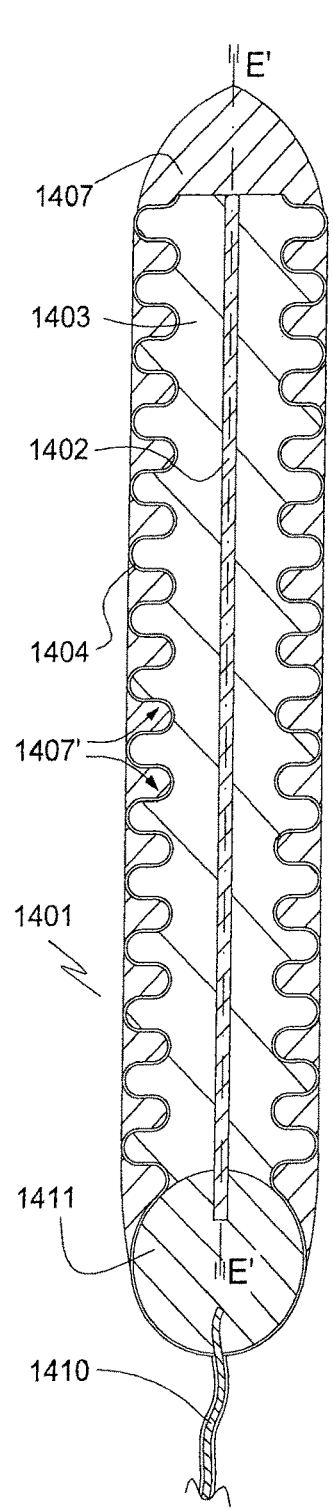
FIGS. 18a, 18b further embodiments of the proto electrode of the invention, in the same view as in FIG. 17d.

The proto electrode 1401 of FIG. 18a differs from that of FIG. 17d by the indentations 1407' of the bellows shaped second coat 1404 being filled with cap material 1407 soluble in aqueous body fluid. Thereby the friction between the proto electrode and soft tissue during insertion is substantially reduced. If desired, a material different from that of the cap 1407 can be used for filling the indentations 1407' such as, for instance, the material of the first coat.

Figure 18B:
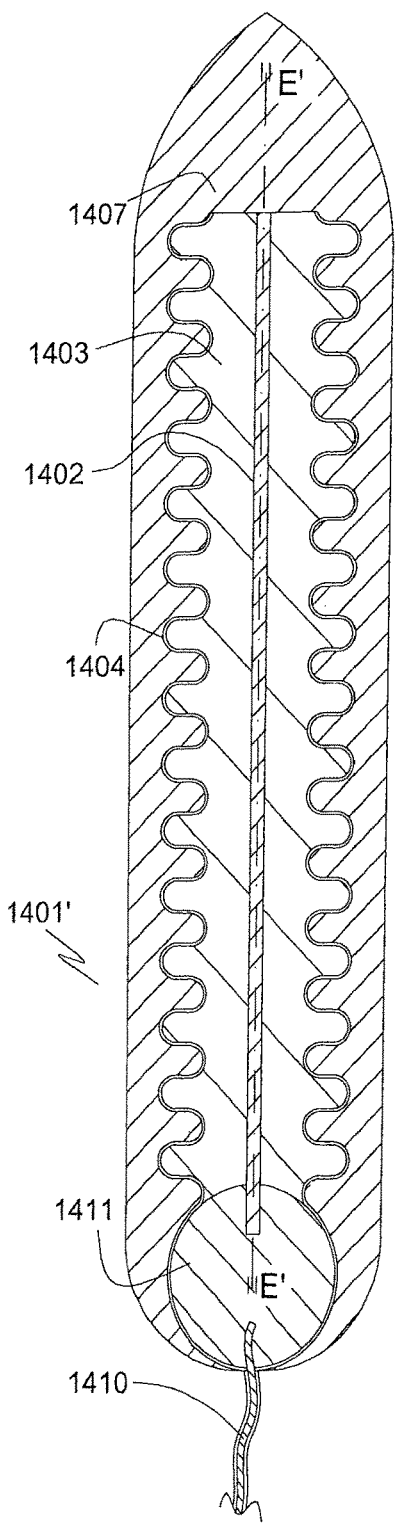

The proto electrode 1401' of FIG. 18b differs from that of FIG. 18a by cap 1407 material not only by filling the indentations 1407 but by embedding the portions of the proto electrode covered by the second coat. The proto electrode 1401' thereby is reinforced and can be inserted into soft tissue at a minimal risk of breaking. Elements identified by reference numbers 1502, 1503, 1510, and 1511 correspond to those identified by reference numbers 1302, 1303, 1310, and 1311 in FIG. 17d. The proto electrode 1501 is rotationally symmetric in respect of its central axis E'-E'.

Elements identified by reference numbers 1402, 1403, 1410, and 1411 correspond to those identified by reference numbers 1302, 1303, 1310, and 1311 in FIG. 17d. The proto electrodes 1401, 1401' are rotationally symmetric in respect of their central axis E'-E'.

Variation of the First Stage Proto Electrode of FIG. 17d

The rotationally symmetric prestage electrode 1501 of FIG. 19a corresponds to the prestage electrode of FIG. 17d except for the radial cutting plane A"-A" perpendicular to the electrode long axis F'-F' being disposed distally of the front end of the electrode body 1502. Cutting the prestage electrode 1501 in this plane produces the proto electrode 1501' with a flat front face 1506, which differs from the corresponding proto electrode 1301" of FIG. 17c by the distal end of the electrode body 1502 being offset in a proximal direction for a short distance from the cutting plane A"-A"/front face 1506 and being fully embedded in the first coat 1503. Thereby the electrode body of the corresponding electrode of the invention is arranged withdrawn by a distance h into the inner space defined by bellows formed second coat 1504. The effect of this is that the front end of the electrode body 1502 is additionally shielded from contact with adjacent soft tissue, and the tissue so protected from heat generated at the front end of the electrode body 1502. Elements identified by reference numbers 1510 and 1511 correspond to elements 1310, 1311 in FIGS. 17*c*, 17*d*.

Materials

Electrode Body.

The electrode body is preferably of a noble metal or an alloy of noble metals or comprising noble metals such as gold, silver, platinum, iridium, but other biologically acceptable metals such as stainless steel and tantalum can also be used as well as gold plated copper. Instead of a metal or metal alloy the electrode body may consist of or comprise an electrically conducting polymer but this is not preferred. Alternatively the electrode body can be made of a core of nonconductive polymer material coated with a metal, in particular a noble metal. Portions of the electrode body that are not electrically insulated from tissue fluid upon removal of the first coat may be advantageously provided with surface enlarging elements or structures such as a roughened surface, forests of conducting nanowires, for instance carbon nanowires, or be porous. Surface enlarging structures of this kind will reduce the impedance of the electrode body. The electrical connection of the electrode body with a control unit can be provided by a separate electrical conductor coupled between the rear end of the electrode and the control unit or by the electrode body itself, a rear section thereof functioning as a coupling conductor. In such case the rear section as to be electrically insulated.

First Coat. The electrode of the invention is embedded in/coated with one or more biocompatible first coat materials, which may be water dissolvable, swellable and/or degradable. If embedded in two or more of such materials they differ in their dissolution rate. Preferred first coat materials are water soluble carbohydrates and proteins as well as mixtures thereof. However, it is also possible to use water insoluble polymer materials swellable in water and/or degradable in body fluid. A suitable first coat material of which the dissolution dime can be controlled is obtained by repeatedly boiling and cooling an aqueous solution of a sugar or a mixture of sugars selected from sucrose, lactose, mannose, maltose and an organic acid selected from citric acid, malic acid, phosphoric acid, tartaric acid. By selecting particular combinations of sugar(s) and organic acid(s) it is possible to obtain materials with different dissolution times. Gelatin may also be used as a first coat material. It is well known that different types of gelatin or gelatin based materials have different dissolution rates. If the first coat of water soluble or swellable material comprises two or more sections disposed along the electrode body, the selection of a proper combination of gelatins provides a distal first coat section of shorter dissolution time and a proximal first coat section of longer dissolution time. The use of a sugar-based first coat material for the distal first coat section and of a gelatin-based first coat material for the proximal first coat section or vice versa is also possible, as well as the use of gelatin for a distal first coat section and of gum arabic for a first coat proximal section. The selection of further useful combinations of first coat materials, such as various types of natural gums, is within the easy reach of a person skilled in the art. Optionally, first coat materials with substantially longer dissolution times, such as modified collagen, cellulose derivatives, modified starch or other biocompatible materials, such as poly-glycolic acid can also be used.

Second Coat. In principle, polymer materials of all kinds suitable for electrical insulation can be used. However, the tiny structure of the precursor microelectrode of the invention to be produced by polymer coating restricts the number of application methods and useful polymers. While deposition of monomer from the gas phase is preferred, such as for providing a parylene coat, dipping of the electrode body coated with water soluble/swellable/degradable first coat material into a polymer or prepolymer solution, withdrawing it from the solution, and evaporating the solvent, optionally allowing a prepolymer to settle, is also useful. The dipping method should take recourse to a polymer solvent that does not interact with the water soluble/swellable/degradable material, in particular a non-polar solvent such as an alkane or alkene or cycloalkane or a non-polar aromatic solvent or a mixture thereof, in particular pentane or hexane but also diethyl ether or dichloromethane. Suitable polymers comprise biocompatible types of polyurethane, polyurethane urea and polyimide.

Optionally the polymer insulating coat of the proto electrode, the proto electrode bundle or proto electrode array of the invention or a shell of water dissolvable material on that coat can be covered, completely or in part, by a biocompatible gliding agent to reduce friction during insertion into tissue. Useful gliding agents include glycerol monopalmitate, glycerol dipalmitate, glycerol monostearate, glycerol distearate, palmityl alcohol, stearyl alcohol. A thin coat of gliding agent can be applied by, for instance, spraying with a solution of the agent in ethanol or ethyl acetate.

Electrode Bundles. A bundle of proto electrodes of the invention can be bundled in different ways, such as by incorporation of their rear end portions in a base of polymer or other material or by joining their rear end portions with a glue. The bundling can be temporary, such as for keepings the electrodes in a fixed relationship prior to and during insertion into soft tissue, or permanent.

A water dissolvable or degradable glue or a base of corresponding properties allows the proto electrodes or electrodes to dissociate quickly or slowly upon insertion. A swellable but not water soluble glue or base material will allow the inserted proto electrodes and the electrodes of the invention formed from them to be displaced in a restricted manner while an insoluble and non-swellable glue or base material will restrain their movement to bending and, if designed extendable, to changes in length.

The individual electrodes of an electrode bundle of the invention may differ in length. For instance, a central electrode of a bundle may be longer than peripheral electrodes thereof to provide a central bundle point.

Upon insertion into soft tissue, the proto electrodes of the proto electrode bundle are transformed to electrodes of the invention and the proto electrode bundle thereby is transformed to an electrode bundle of the invention.

Electrode Arrays. In this application an electrode or electrode bundle array is a device comprising a pattern of two or more proto electrodes or proto electrode bundles of the invention disposed on and attached to at least one face of an electrically non conducting support. An electrode or electrode bundle array may also comprise embodiments of the invention other than electrodes, such as semiconductor elements illustrated in FIGS. 15*a*, 16*a*. Thin supports of a suitable polymer like polypropylene, polyacrylate, polycarbonate and parylene C comprising substantially only two faces are preferred. The supports can be flat but also curved. The electrodes can be mounted on both surfaces of the support. The proto electrodes and the proto electrodes of electrode bundles attached to the support protrude from the support at an angle, in particular an angle of from about 15° to about 75° and even to about 90° included by the proto electrode or proto electrode bundle long axis and its projection onto the mounting face of the support and/or at an angle of from about 15° to about 75° included by the proto electrode or proto electrode bundle long axis and a central long axis of the support. The support may contain pores or be semipermeable to body fluids, that is, permeable to at least water and salts.

Upon insertion into soft tissue, the proto electrodes of the proto electrode array are transformed to electrodes of the invention and the proto electrode array thereby is transformed to an electrode array of the invention.

The support of an electrode array of the invention can be of a material which is soluble or degradable in soft tissue. Useful materials comprise those identified above as useful water soluble/swellable/degradable first coat materials.

The electrode array support can be equipped with a control unit, such as one comprising or consisting of an electronic chip in electric contact with the individual electrode conductors. The control unit can comprise or be in electrical contact with a unit for electric tissue stimulation and/or signal amplifier(s) for recording electrical nerve signals.

What is claimed is:

1. Proto microelectrode from which a micro electrode is formed in situ upon insertion of the proto microelectrode into soft tissue, comprising a flexible oblong electrode body of electrically conducting material having a front distal end and a rear proximal end, the electrode body comprising one or more of a metal or a metal alloy or an electrically conducting form of carbon or an electrically conducting polymer or a combination thereof, a first coating comprising one or more of a water soluble material and/or a swellable material and/or a degradable material on the electrode body and having a length that extends along the electrode body at least over a portion extending from its front end towards its rear end, and a second coating of electrically insulating, water insoluble flexible polymer material on the first coating and at least along the length of the first coating, the second coating comprising one or more through openings at or near its front end to permit the first coating to dissolve, swell, or degrade when the microelectrode is inserted into the soft tissue.

2. The proto microelectrode of claim 1, wherein the material of the first coating is one or more of the following: readily soluble in aqueous body fluid, such as glucose, or one which is not readily soluble in aqueous body fluid, such as glucose acetate, or one of intermediate solubility, such as partially acetylated glucose.

3. The proto microelectrode of claim 2, wherein the material of the first coating is a combination of two or more materials of different solubility and/or dissolution rate.

4. The proto microelectrode of claim 3, wherein said combination is one of low molecular carbohydrate and of peptide or protein.

5. The proto microelectrode of claim 1, wherein surface areas of the first coating not covered by the second coating are coated with a third coating of a biocompatible material soluble in aqueous body fluid, said third coating retarding access of aqueous body fluid to the first coating.

6. The proto microelectrode of claim 5, wherein the third coating material is selected from the group consisting of shellack, Kollicoat® IR, a material capable of forming a gel at contact with aqueous body fluid, such as gelatin or a cellulose derivative such as hydroxypropylmethyl cellulose, gelatin cross-linked with 1-(3-dimethylaminopropyl)-3-ethylcarbodiimide, and other cross-linkedmaterials of similar physical properties.

7. The proto microelectrode of claim 1, wherein the front end of the electrode body coincides with the front end of the first coating and of the second coating.

8. The proto microelectrode of claim 1, wherein the electrode body is electrically connected with a control unit by means of an electrical conductor.

9. The proto microelectrode of claim 1, wherein the electrode body comprises at its rear end a device for wireless communication with a control unit.

10. The proto microelectrode of claim 1, wherein the material of the second coating has a wall thickness that is substantially smaller than the diameter of the electrode body and the wall thickness of the first coating by a factor of five or ten or more.

11. The proto microelectrode of claim 1, wherein the diameter of the electrode body is from 1 μm to 100 μm, and wherein the wall thickness of the second coating is from 2 μm up to 20 μm or more.

12. The proto microelectrode of claim 1, wherein the material of the second coating is selected from one of the following: Parylene, in particular of Parylene C, teflon, polyurethane, polyimide, various kinds of silicones, and synthetic or natural rubber.

13. The proto microelectrode of claim 1 comprising one or more anchoring elements.

14. The proto microelectrode of claim 13, wherein said two or more adjacent sections differ in one or more of their solubility and/or swelling and/or degradation properties in aqueous body fluid and/or in their content of one or more pharmacologically active agents.

15. The proto microelectrode of claim 14, wherein said one or more pharmacologically active agents is/are chosen from the group comprising agents influencing the function of nerve synapses, neuroleptics, sedatives, analgesics, agents exerting a trophic effect on nerve cells, gene vectors for long term effect, anti-inflammatory agents, anticoagulants, β-receptor blockers, antibodies and nutrients.

16. The proto microelectrode of claim 1, wherein the first coating comprises two or more adjacent sections extending along the electrode body.

17. The proto microelectrode of claim 1, wherein the first coating or a section thereof comprises one or more pharmacologically active ingredients.

18. The proto microelectrode of claim 1, wherein the second coating comprises a bellows shaped portion, said portion being optionally electrically shielded.

19. The proto microelectrode of claim 1, wherein the electrode body is made of a nonconductive polymer material coated with a metal, in particular a noble metal.

20. The proto microelectrode of claim 1, further comprising a drug reservoir compartment disposed at its rear end or proximal to its front end, arranged such that, when said proto microelectrode is inserted in situ in soft tissue, said drug reservoir compartment is, at its front end, in fluid communication with a tubular column of body fluid accumulated in the interstice between the electrode body and the second coating, and wherein said drug reservoir compartment is optionally connected, at its rear end, to a conduit through which aqueous fluid can be adduced to the compartment.

21. The proto microelectrode of claim 20, wherein said aqueous fluid comprises a pharmacologically active agent.

22. Proto microelectrode bundle comprising at least two proto microelectrodes according to claim 1.

23. Proto microelectrode array comprising at least two proto microelectrodes according to claim 1.

24. Microelectrode formed from the proto microelectrode of claim 1 by contact with body fluid, comprising a flexible oblong electrode body of electrically conducting material having a front distal end and a rear proximal end, the electrode body comprising one or more of a metal or a metal alloy or an electrically conducting form of carbon or an electrically conducting polymer or a combination thereof, and a coating of electrically insulating, water insoluble flexible polymer material extending along a portion of the electrode body from the front end thereof towards the rear end thereof interspaced from the electrode body by a tubular layer of body fluid.

25. Microelectrode bundle comprising at least two microelectrodes according to claim 24.

26. Microelectrode array comprising at least two microelectrodes according to claim 24.

27. Microelectrode formed from the proto microelectrode of claim 1 by contact with body fluid, comprising a flexible oblong electrode body of electrically conducting material having a front distal end and a rear proximal end, the electrode body comprising one or more of a metal or a metal alloy or an electrically conducting form of carbon or an electrically conducting polymer or a combination thereof, and a coating of electrically insulating, water insoluble flexible polymer material extending along a portion of the electrode body from the front end thereof towards the rear end thereof interspaced from the electrode body by a tubular layer of a gel formed by contact of body fluid with a gelling agent.

28. Proto microelectrode from which a micro electrode is formed in situ upon insertion of the proto microelectrode into soft tissue, comprising a flexible oblong electrode body of electrically conducting material having a front distal end and a rear proximal end, the electrode body comprising one or more of a metal or a metal alloy or an electrically conducting form of carbon or an electrically conducting polymer or a combination thereof, a first coating comprising one or more of a water soluble material and/or a swellable material and/or a degradable material on the electrode body having a length that extends along the electrode body at least over a portion extending from its front end towards its rear end, and a second coating of electrically insulating, water insoluble flexible material on the first coating and at least along the length of the first coating, the second coating comprising one or more through openings at or near its front end to permit the first coating to dissolve, swell, or degrade when the microelectrode is inserted into the soft tissue, wherein the second coating is configured to flex with the electrode, and is configured to move with the tissue in which it is received after the first coating is dissolved, swollen or degraded.

* * * * *